(12) United States Patent
Davies et al.

(10) Patent No.: US 8,347,879 B2
(45) Date of Patent: *Jan. 8, 2013

(54) FLUID DISPENSING DEVICE

(75) Inventors: Michael Birsha Davies, Ware (GB);
James W. Godfrey, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1425 days.

This patent is subject to a terminal disclaimer.

(21) Appl. No.: 10/513,201

(22) PCT Filed: May 7, 2003

(86) PCT No.: PCT/EP03/04858
§ 371 (c)(1),
(2), (4) Date: Nov. 2, 2004

(87) PCT Pub. No.: WO03/095007
PCT Pub. Date: Nov. 20, 2003

(65) Prior Publication Data
US 2005/0224525 A1    Oct. 13, 2005

(30) Foreign Application Priority Data

May 9, 2002 (GB) .................................. 0210605.2
Aug. 1, 2002 (GB) .................................. 0217798.8
Aug. 21, 2002 (GB) ................................. 0219462.9

(51) Int. Cl.
*A61M 11/00* (2006.01)
*A61M 11/08* (2006.01)

(52) U.S. Cl. ......... 128/200.23; 128/200.14; 128/200.21; 128/200.22; 128/913

(58) Field of Classification Search ............. 128/200.14, 128/200.22, 200.23, 200.21, 913
See application file for complete search history.

(56) References Cited

U.S. PATENT DOCUMENTS

| | | | |
|---|---|---|---|
| 2,602,569 A | 7/1952 | Ryan | |
| 2,673,008 A | 3/1954 | Ryan | |
| 2,904,223 A | 9/1959 | Ryan | |
| 3,237,809 A | 3/1966 | Daragan et al. | |
| 3,272,391 A | 9/1966 | Meshberg | |
| 3,405,843 A * | 10/1968 | Watson, Jr. ...................... | 222/95 |

(Continued)

FOREIGN PATENT DOCUMENTS
AU       2004218872 B1    9/2004
(Continued)

OTHER PUBLICATIONS

Ludovic et al., FR2812626A1, Feb. 15, 2002, English translation provided by The European Patent Office, Description and claims.*

(Continued)

*Primary Examiner* — Clinton T Ostrup
(74) *Attorney, Agent, or Firm* — James P. Riek

(57) ABSTRACT

A fluid dispensing device is disclosed having a housing and a fluid discharge device. The fluid discharge device is arranged to be actuated by one or more levers so as to apply a force transversely to the fluid discharge device which is used to move a container forming part of the fluid discharge device along a longitudinal axis of the fluid discharge device to cause actuation of a pump forming part of the fluid discharge device. A pre-load means is used to prevent actuation of the pump until a pre-determined force is applied to each lever of sufficient magnitude to guarantee the production of a well developed efficient spray from the fluid dispensing device.

45 Claims, 13 Drawing Sheets

U.S. PATENT DOCUMENTS

| | | | |
|---|---|---|---|
| 3,516,424 | A | 6/1970 | Eagle |
| 4,083,476 | A | 4/1978 | Schwartz et al. |
| 4,111,338 | A | 9/1978 | Cheng et al. |
| 4,132,359 | A | 1/1979 | Nozawa |
| 4,155,487 | A | 5/1979 | Blake |
| 4,185,776 | A | 1/1980 | Nozawa |
| 4,223,812 | A | 9/1980 | van Lit |
| 4,402,430 | A | 9/1983 | Fox et al. |
| 4,648,393 | A | 3/1987 | Landis et al. |
| 4,678,106 | A | 7/1987 | Newell et al. |
| 4,765,515 | A | 8/1988 | Lippman |
| 4,771,769 | A | 9/1988 | Hegemann et al. |
| 4,807,786 | A | 2/1989 | Gueret |
| 4,860,738 | A | 8/1989 | Hegemann et al. |
| 4,921,142 | A | 5/1990 | Graf et al. |
| 4,944,429 | A | 7/1990 | Bishop et al. |
| 4,946,069 | A | 8/1990 | Fuchs |
| 5,062,549 | A | 11/1991 | Smith et al. |
| 5,190,029 | A | 3/1993 | Bryon et al. |
| 5,273,189 | A | 12/1993 | Jouillat et al. |
| 5,487,489 | A | 1/1996 | Weiss et al. |
| 5,568,884 | A | 10/1996 | Bruna |
| 5,709,325 | A | 1/1998 | Renault et al. |
| 5,899,365 | A | 5/1999 | Hochrainer et al. |
| 6,055,979 | A | 5/2000 | Fuchs |
| 6,152,330 | A | 11/2000 | Polan |
| 6,189,739 | B1 | 2/2001 | Von Schuckmann |
| 6,237,812 | B1 | 5/2001 | Fukada |
| 6,257,457 | B1 | 7/2001 | Oechsel |
| 6,261,274 | B1 | 7/2001 | Arghyris et al. |
| 6,302,101 | B1 | 10/2001 | Py |
| 6,305,371 | B1 | 10/2001 | Frid et al. |
| 6,315,165 | B1 * | 11/2001 | Regan .................. 222/103 |
| 6,338,422 | B1 | 1/2002 | DeJonge |
| 6,364,166 | B1 | 4/2002 | Ritsche et al. |
| 6,382,205 | B1 | 5/2002 | Weinstein et al. |
| 6,382,465 | B1 | 5/2002 | Greiner-Perth |
| 6,419,124 | B1 * | 7/2002 | Hennemann et al. ...... 222/321.6 |
| 6,484,715 | B1 | 11/2002 | Ritsche et al. |
| 6,527,144 | B2 | 3/2003 | Ritsche et al. |
| 6,568,389 | B1 | 5/2003 | Rand et al. |
| 6,578,741 | B2 | 6/2003 | Ritsche et al. |
| 6,644,305 | B2 | 11/2003 | MacRae et al. |
| 6,745,760 | B2 * | 6/2004 | Grychowski et al. .... 128/200.14 |
| 6,750,210 | B2 | 6/2004 | Biggadike |
| 6,860,411 | B2 | 3/2005 | Stradella |
| 7,108,159 | B2 | 9/2006 | Stradella |
| 7,353,971 | B2 | 4/2008 | Stradella |
| 7,854,352 | B2 | 12/2010 | Davies et al. |
| 2001/0013343 | A1 | 8/2001 | Andersson |
| 2002/0008122 | A1 * | 1/2002 | Ritsche et al. ............ 222/383.3 |
| 2002/0011530 | A1 | 1/2002 | Fuchs |
| 2002/0117513 | A1 | 8/2002 | Helmlinger |
| 2002/0170928 | A1 | 11/2002 | Grychowski et al. |
| 2003/0052196 | A1 | 3/2003 | Fuchs |
| 2003/0100867 | A1 | 5/2003 | Fuchs |
| 2004/0245291 | A1 | 12/2004 | Simon et al. |
| 2005/0040188 | A1 | 2/2005 | Herry et al. |
| 2005/0072861 | A1 | 4/2005 | Petit |
| 2005/0098175 | A1 * | 5/2005 | Stradella .................. 128/202.17 |
| 2005/0211241 | A1 | 9/2005 | Anderson et al. |
| 2005/0234402 | A1 | 10/2005 | Collins et al. |
| 2005/0258191 | A1 | 11/2005 | Davies |
| 2006/0108378 | A1 | 5/2006 | Cohen et al. |
| 2006/0191959 | A1 | 8/2006 | Davies et al. |
| 2007/0056585 | A1 | 3/2007 | Davies et al. |
| 2007/0095853 | A1 | 5/2007 | Bonney et al. |
| 2007/0131717 | A1 | 6/2007 | Davies et al. |
| 2007/0138207 | A1 | 6/2007 | Bonney et al. |

FOREIGN PATENT DOCUMENTS

| | | |
|---|---|---|
| DE | 2633901 A1 | 2/1977 |
| DE | 19610456 | 9/1997 |
| EP | 0412524 A1 | 2/1991 |
| EP | 0461277 B1 | 12/1991 |
| EP | 1129786 A2 | 9/2001 |
| EP | 1281443 A2 | 2/2003 |
| FR | 1444387 | 7/1966 |
| FR | 2570000 A1 | 3/1986 |
| FR | 2671294 A1 | 7/1992 |
| FR | 2807954 | 10/2001 |
| FR | 2812826 | 2/2002 |
| FR | 2817245 A1 * | 5/2002 |
| FR | 2830519 | 4/2003 |
| GB | 173123 | 12/1921 |
| GB | 659132 | 10/1951 |
| GB | 906837 A | 9/1962 |
| GB | 1097254 | 1/1968 |
| GB | 1481199 A | 7/1977 |
| GB | 2251898 | 7/1992 |
| JP | 04057264 U | 2/1992 |
| JP | 09225363 A | 9/1997 |
| JP | 09313998 A | 12/1997 |
| JP | 10001155 | 1/1998 |
| JP | 10179739 A | 7/1998 |
| JP | 10179739 A1 | 7/1998 |
| JP | 2000355382 A | 12/2000 |
| WO | 9405593 A1 | 3/1994 |
| WO | 9411115 A1 | 5/1994 |
| WO | 9901229 A1 | 1/1999 |
| WO | 9938555 A1 | 8/1999 |
| WO | 9949984 A1 | 10/1999 |
| WO | WO 00/07740 | 2/2000 |
| WO | 0018458 A1 | 4/2000 |
| WO | 0136018 A2 | 5/2001 |
| WO | 0220168 A1 | 3/2002 |
| WO | WO 02/20370 | 3/2002 |
| WO | 0249698 A1 | 6/2002 |
| WO | WO 0244056 A1 * | 6/2002 |
| WO | WO 02053294 A1 * | 7/2002 |
| WO | 03020350 A1 | 3/2003 |
| WO | 03026803 A1 | 4/2003 |
| WO | 03026804 A1 | 4/2003 |
| WO | 03026805 A1 | 4/2003 |
| WO | WO 03/029105 | 4/2003 |
| WO | WO 03029105 A1 * | 4/2003 |
| WO | 03043909 A2 | 5/2003 |
| WO | 03061843 A1 | 7/2003 |
| WO | 03095006 A2 | 11/2003 |
| WO | 03095007 A2 | 11/2003 |
| WO | 2004013009 A1 | 2/2004 |
| WO | 2004080606 A1 | 9/2004 |
| WO | 2005028007 A1 | 3/2005 |
| WO | 2005087615 A1 | 9/2005 |
| WO | 2006109021 A1 | 10/2006 |

OTHER PUBLICATIONS

Patent Abstracts of Japan, 1997(06):JP09048455 (Feb. 18, 1997).
U.S. Appl. No. 10/523,163—Office Action dated Jun. 25, 2007.
U.S. Appl. No. 10/523,163—Notice of Allowance dated Jul. 28, 2008.
U.S. Appl. No. 10/523,163—Office Action dated Nov. 17, 2008.
U.S. Appl. No. 10/523,163—Final Office Action dated May 29, 2009.
Amendment filed Dec. 20, 2007 in response to Non-Final Rejection issued Jun. 25, 2007 for U.S. Appl. No. 10/523,163.
Notice of Allowance issued Feb. 8, 2008 for U.S. Appl. No. 10/523,163.
Examiner Interview Summary Record issued Feb. 8, 2008 for U.S. Appl. No. 10/523,163.
Request for Continued Examination (RCE) with IDS filed May 8, 2008 for U.S. Appl. No. 10/523,163.
Request for Continued Examination (RCE) with IDS filed Oct. 28, 2008 for U.S. Appl. No. 10/523,163.
Amendment filed May 12, 2009 in response to Non-Final Rejection issued Nov. 17, 2008 for U.S. Appl. No. 10/523,163.
U.S. Appl. No. 10/577,977, filed Nov. 2, 2004.
Non-Final Rejection issued Sep. 18, 2009 for U.S. Appl. No. 10/577,977.
Amendment filed Jan. 18, 2010 in response to Non-Final Rejection issued Sep. 18, 2009 for U.S. Appl. No. 10/577,977.
Notice of Allowance issued Apr. 21, 2010 for U.S. Appl. No. 10/577,977.

Request for Continued Examination (RCE) with Amendment and IDS filed Jul. 19, 2010 for U.S. Appl. No. 10/577,977.
Notice of Allowance issued Aug. 6, 2010 for U.S. Appl. No. 10/577,977.
Request for Continued Examination (RCE) with Amendment and IDS filed Nov. 8, 2010 for U.S. Appl. No. 10/577,977.
U.S. Appl. No. 10/598,464, filed Mar. 10, 2005.
Non-Final Rejection issued Aug. 6, 2009 for U.S. Appl. No. 10/598,464.
Amendment filed Nov. 3, 2009 in response to Non-Final Rejection issued Aug. 6, 2009 for U.S. Appl. No. 10/598,464.
Non-Final Rejection issued Mar. 1, 2010 for U.S. Appl. No. 10/598,464.
Amendment filed Jun. 1, 2010 in response to Non-Final Rejection issued Mar. 1, 2010 for U.S. Appl. No. 10/598,464.
Non-Final Rejection and claim set for co-pending U.S. Appl. No. 11/911,060 (for obviousness-type double patenting) issued Sep. 3, 2010 for U.S. Appl. No. 10/598,464.
Amendment filed Dec. 14, 2010 in response to Non-Final Rejection issued Sep. 3, 2010 for U.S. Appl. No. 10/598,464.
Ex Parte Quayle Action issued Jan. 25, 2011 for U.S. Appl. No. 10/598,464.
Response to Ex Parte Quayle Action filed Mar. 25, 2011 for U.S. Appl. No. 10/598,464.
Notice of Allowance issued May 26, 2011 for U.S. Appl. No. 10/598,464.

U.S. Appl. No. 11/911,060, filed May 27, 2008.
Office Action dated Sep. 8, 2008 for U.S. Appl. No. 11/911,060.
Amendment filed Mar. 9, 2009 in response to Office Action dated Sep. 8, 2008 for U.S. Appl. No. 11/911,060.
Final Office Action dated May 14, 2009 for U.S. Appl. No. 11/911,060.
Request for Continued Examination (RCE) with Amendment and IDS filed Jul. 15, 2009 for U.S. Appl. No. 11/911,060.
Office Action dated Aug. 7, 2009 for U.S. Appl. No. 11/911,060.
Amendment filed Feb. 4, 2010 in response to Office Action dated Aug. 7, 2009 for U.S. Appl. No. 11/911,060.
Final Office Action dated May 13, 2010 for U.S. Appl. No. 11/911,060.
Request for Continued Examination (RCE) with Amendment and IDS filed Jul. 13, 2010 for U.S. Appl. No. 11/911,060.
Terminal Disclaimer filed Jul. 13, 2010 in response to Final Office Action dated May 13, 2010 for U.S. Appl. No. 11/911,060.
U.S. Appl. No. 10/548,716, filed Sep. 8, 2005.
U.S. Appl. No. 10/572,916, filed Nov. 1, 2006.
Proprietary Lab Notebook, pp. 2-27 (with entry dates and notebook No. redacted) entered by inventor, M. Davies, on or before May 7, 2003 filed of PCT/EP2003/004858, a PCT application from which U.S. Appl. No. 10/513,201 claims priority.

* cited by examiner

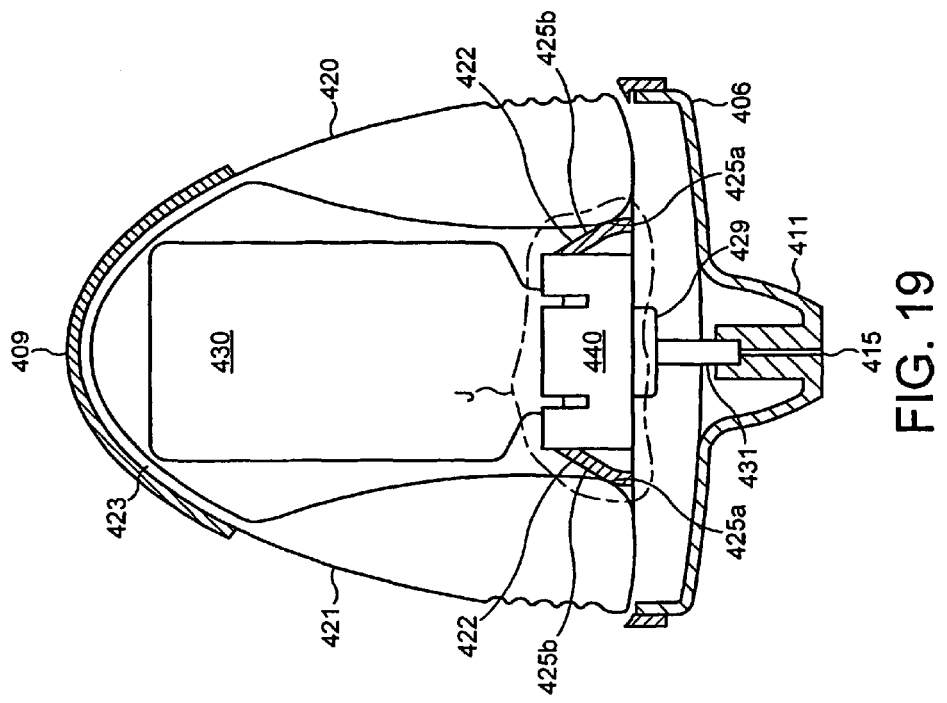
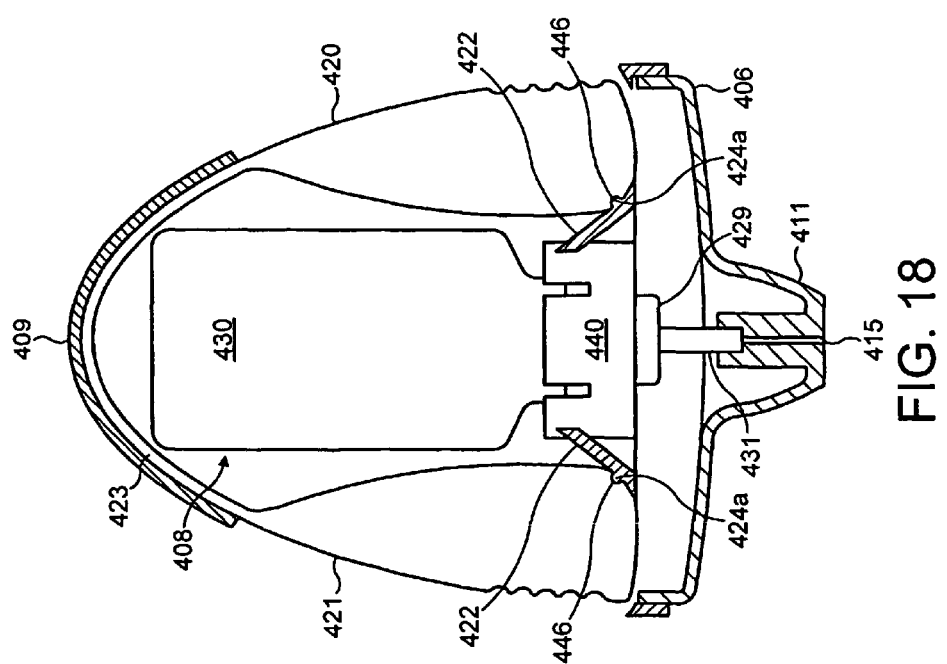

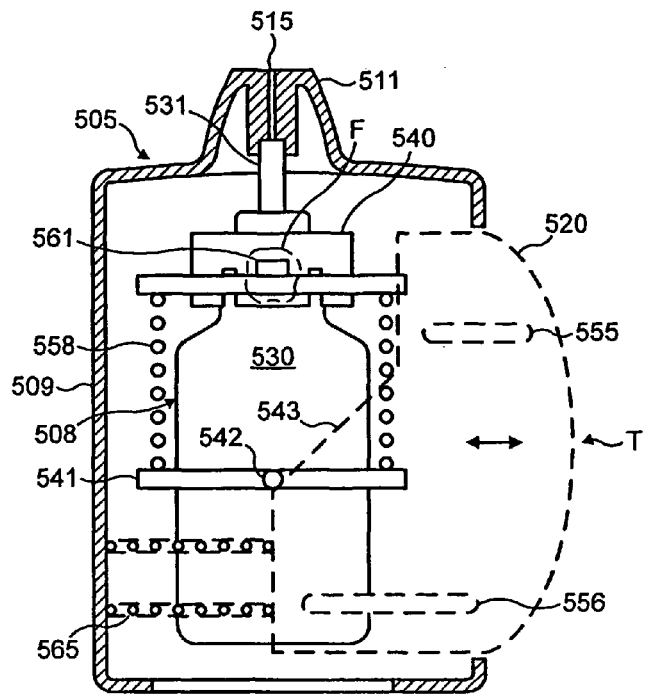
FIG. 22
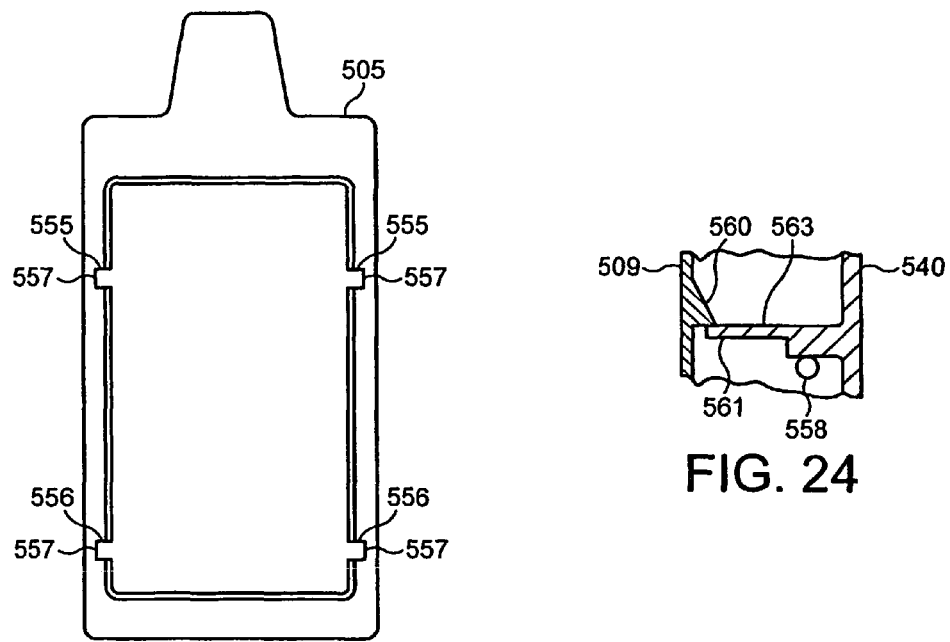
FIG. 23
FIG. 24

FLUID DISPENSING DEVICE

CROSS-REFERENCE TO RELATED APPLICATIONS

This application is filed pursuant to 35 USC 371 as a United States National Phase Application of International Patent Application Serial No. PCT/EP03/04858 filed on 7 May 2003, which claims priority from GB 0210605.2 filed on 9 May 2002, GB 0217798.8 filed on 1 Aug. 2002, and 0219462.9 filed on 21 Aug. 2002, all in the United Kingdom.

FIELD OF THE INVENTION

The present invention relates to a medicament dispenser and in particular to a fluid dispensing device for use as a nasal inhaler.

BACKGROUND OF THE INVENTION

It is known to provide a medicament dispenser, in which fluid spray is dispensed via a nozzle or orifice upon the application of a force by a user to an actuation lever or button. Such devices may be arranged to dispense a single dose or may alternatively be arranged with a reservoir containing several doses to be dispensed.

It is a problem with such a prior art sprays that if the actuator is moved in a slow or unpredictable manner a strong and well defined spray may not be produced and so the medicament may not be effectively dispensed. This problem is particularly significant where an actuator (e.g. a lever) acts on a pump mechanism such as to pump the fluid to be sprayed from a container. In this case, slow or unpredictable actuation results in a slow or unpredictable actuation of the pump and hence, and unreliable spray characteristics. By way of a solution to this problem, the dispensing device herein includes a 'commitment' feature, which prevents actuation of the pump in the absence of the application of pre-determined force to a finger operable actuator.

It is an object of this invention to provide a fluid dispensing device that is easier to use and in particular a device which provides a more efficient dispensing of fluid.

SUMMARY OF THE INVENTION

According to a first aspect of the invention there is provided a fluid dispensing device for spraying a fluid into a body cavity comprising a housing, a nozzle for insertion into a body cavity, a fluid discharge device moveably housed within the housing, the fluid discharge device having a longitudinal axis and comprising a container for storing the fluid to be dispensed and a compression pump having a suction inlet located within the container and a discharge tube extending along the longitudinal axis for transferring fluid from the pump to the nozzle and finger operable means moveable transversely with respect to the longitudinal axis of the fluid discharge device to apply a force to the container to move the container along the longitudinal axis towards the nozzle so as to actuate the compression pump wherein a pre-load means is provided to prevent actuation of the compression pump until a pre-determined force is applied to the finger operable means.

The term finger operable means is meant to encompass such means operable by action of the finger or thumb, or combinations thereof of a typical user (e.g. an adult or child patient).

The finger operable means is moveable transversely with respect to the longitudinal axis of the fluid discharge device to apply a force directly or indirectly to the container. In alternative aspects, the finger operable means may therefore contact the container or be coupled thereto to enable the necessary transfer of force.

Suitably, the finger operable means is arranged to apply mechanical advantage. That is to say, the finger operable means applies mechanical advantage to the user force to adjust (generally, to enhance or smooth) the force experienced by the container. The mechanical advantage may in one aspect, be provided in either a uniform manner such as by a constant mechanical advantage enhancement, for example by a ratio of from 1.5:1 to 10:1 (enhanced force:initial force), more typically from 2:1 to 5:1. In another aspect, the mechanical advantage is applied in a non-constant manner such as progressive increase or progressive decrease of mechanical advantage over the applied force cycle. The exact profile of mechanical advantage variation may be readily determined by reference to the desired spray profile and all relevant characteristics of the device and formulation to be sprayed (e.g. viscosity and density).

Suitably, the finger operable means has a form, which naturally gives rise to mechanical advantage such as a lever, cam or screw form.

The finger operable means may comprise of at least one lever pivotally connected to part of the housing and arranged to transfer force to the container (e.g. acting directly thereupon) so as to urge the container towards the nozzle when the or each lever is moved by a user.

In one aspect, there are two opposing levers, each of which pivotally connect to part of the housing and may be arranged to act upon the container so as to urge the container towards the nozzle when the two levers are squeezed together by a user.

Alternatively, the finger operable means may comprise of at least one lever to apply a force to an actuating means used to move the container towards the nozzle so as to actuate the pump.

In which case the or each lever may be pivotally supported at a lower end within the housing and the actuating means may in aspects be connected to a neck of the container (e.g. formed as a collar thereto).

Suitably, there may be two opposing levers, each of which is pivotally supported near a lower end of the housing and may be arranged to act upon the actuating means so as to urge the container towards the nozzle when the two levers are squeezed together by a user.

Alternatively, the finger operable means may comprise of at least one lever slidably supported within the housing to apply a force to the container so as to move the container towards the nozzle and actuate the compression pump.

The pre-load means acts such as to prevent actuation of the compression pump until a pre-determined force is applied to the finger operable means. The pre-determined force may thus, be thought of as a 'threshold' or 'barrier' force which must first be overcome before actuation of the compression pump can occur.

The quantum of pre-determined force that is to be overcome before actuation of the compression pump is enabled is selected according to various factors including characteristics of the pump, typical user profile, nature of the fluid and the desired spray characteristics.

Typically, the pre-determined force is in the range from 5 to 30N, more typically from 10 to 25N. That is to say, typically from 5 to 30N, more typically from 10 to 25N of force must be applied to the finger operable means before actuation of the compression pump is enabled. Such values tend to correspond to a force which prevents a suitable 'barrier force' to a weak, nondescript or unintended finger movement whilst readily being overcome by the determined finger (or thumb) action of a user. It will be appreciated that if the device is designed for use by a child or elderly patient it may have a lower pre-determined force than that designed for adult usage.

In accordance with a first embodiment of the invention the pre-load means is physically interposed between the or each finger operable means (e.g. lever) and the container.

In which case, the pre-load means may comprise of a step formed on the container which must be ridden over by the or each lever before the compression pump can be actuated wherein the step is over-ridden when the pre-determined force is applied to the or each lever.

Alternatively, the pre-load means may comprise of a step formed on the or each finger operable means (e.g. lever) which must be ridden over by the container before the compression pump can be actuated wherein the step is over-ridden when the pre-determined force is applied to the or each lever.

In yet a further alternative, the pre-load means may comprise of at least one detent formed on one of the container or the or each finger operable means (e.g. a lever) and a recess formed on the other of the container or the or each lever wherein the or each detent is able to ride out of the recess with which it is engaged when the pre-determined force is applied to the or each lever.

According to a second embodiment of the invention the pre-load means is interposed between the housing and the container.

In which case, the pre-load means may comprise of one or more detents formed on the container for engagement with part of the housing, the or all of the detents being disengageable from the housing when the pre-determined force is applied to the finger operable means so as to allow the compression pump to be actuated.

Alternatively, the pre-load means may comprise of one or more detents formed on the housing for engagement with part of the container, the or all of the detents being disengageable from the container when the pre-determined force is applied to the finger operable means so as to allow the compression pump to be actuated.

According to a third embodiment of the invention the pre-load means is interposed between the container and the discharge tube.

In which case, the pre-load means may comprises of a step formed on the discharge tube and at least one latching member attached to the container, the arrangement being such that, when the pre-determined force is applied to the finger operable means, the or each latching member is able to ride over the step so as to allow the compression pump to be actuated.

Alternatively, the pre-load means may comprise of a recess formed on the discharge tube and at least one latching member attached to the container, the arrangement being such that, when the pre-determined force is applied to the finger operable means, the or each latching member is able to ride out of the recess so as to allow the compression pump to be actuated.

According to a fourth embodiment of the invention the pre-load means is interposed between the housing and the or each finger operable means (e.g. lever).

In which case, the pre-load means may comprise of at least one detent formed on the housing for engagement with each lever, the or all of the detents being disengageable from the respective lever when the pre-determined force is applied to the or each lever so as to allow the compression pump to be actuated.

Alternatively, the pre-load means may comprise of at least one detent formed on each lever for engagement with part of the housing, the or all of the detents being disengageable from the housing when the pre-determined force is applied to the or each lever so as to allow the compression pump to be actuated.

According to a fifth embodiment of the invention the pre-load means is interposed between the actuating means and the housing.

In which case, the pre-load means may comprise of at least one detent formed on part of the actuating means for engagement with part of the housing, the or all of the detents being disengageable from the housing when the pre-determined force is applied to the or each finger operable means (e.g. lever) so as to allow the compression pump to be actuated.

Alternatively, the pre-load means may comprise of at least one detent formed on part of the housing each detent being arranged for engagement with a complementary recess formed on part of the actuating means, each detent being disengageable from its respective recess when the pre-determined force is applied to the or each finger operable means (e.g. lever) so as to allow the compression pump to be actuated.

According to a sixth embodiment of the invention the pre-load means is interposed between the or each finger operable means (e.g. lever) and the respective actuating means.

In which case, the pre-load means may comprise of at least one detent formed on the or each lever for engagement with a respective recess formed on part of the actuating means, each detent being disengageable from its respective complementary recess when the pre-determined force is applied to the lever so as to allow the compression pump to be actuated.

Alternatively, the pre-load means comprises of at least one detent formed on each actuating means for engagement with a recess formed on a respective lever, each detent being disengageable from its respective complementary recess when the pre-determined force is applied to the lever so as to allow the compression pump to be actuated.

As yet a further alternative, the pre-load means may comprise of an actuating device having a variable mechanical ratio such that until the pre-determined force is applied to the or each finger operable means (e.g. a lever) no significant force is transferred to the container along the longitudinal axis.

The fluid dispensing device may alternatively comprise of a finger operable means in the form of a single lever and the pre-load means may further comprise of a spring interposed between the lever and the container, the spring being used to urge the container towards the nozzle so as to actuate the compression pump.

In which case the spring may be compressed by movement of the lever until the pre-determined force is applied (i.e. by a combination of user-applied force and stored spring force), at which point the threshold of the pre-load means used to prevent actuation of the compression pump is overcome by the force being applied to the container such that the container moves rapidly towards the nozzle so as to actuate the compression pump.

Suitably, the fluid dispensing device is additionally provided with force modifying means for modifying the force applied to the container. That is to say, means for modifying the force applied to (and therefore, ultimately acting on) the container compared to that force directly applied to the finger operable means by the user.

Suitably, the force modifying means acts such as to amplify the force applied (i.e. it comprises force amplifying means). The amplification may be provided in either a uniform manner such as by a constant amplification, for example by a ratio of from 1.5:1 to 10:1 (amplified force:initial force; i.e. degree of amplification of from 1.5 to 10), more typically from 2:1 to 5:1. In another aspect, the amplification is applied in a non-constant manner such as progressive increase or progressive decrease of mechanical advantage over the applied force cycle.

The exact profile of force modification may be readily determined by reference to the desired spray profile and all relevant characteristics of the device and formulation to be sprayed (e.g. viscosity and density).

The force modifying means may in one aspect, be integral with the finger operable means. In this aspect, the force modifying means may comprise an aspect of the finger operable means shaped to give rise to a mechanical advantage (e.g. a lever, cam or screw feature).

In another aspect, the force modifying means is located non-integral with the finger operable means, and typically between the finger operable means and the container. Again this aspect, the force modifying means may comprise an aspect of the finger operable means shaped to give rise to a mechanical advantage (e.g. a lever, cam or screw feature).

In one aspect, the force modifying means only acts (i.e. only acts to modify the user applied force) once the pre-determined force has been overcome. In preferred aspects, the modifying force acts such that once the pre-determined force has been overcome the force applied to the container is either relatively constant or increases on a relatively constant basis.

In one particular aspect, the force modifying means additionally comprises a stop feature, which acts to stop force being applied to the container once either a particular maximum force is reached or more typically, once the container has been moved a particular distance. In one aspect, the stop functions to prevent excess force being applied to the compression pump.

Embodiments are envisaged in which the fluid discharge device is reversibly removable from the housing of the fluid dispensing device. In such embodiments the fluid discharge device comprises a housing assembly and fluid discharge device receivable thereby.

According to another aspect of the present invention there is therefore provided a housing assembly for reversible receipt of a fluid discharge device for spraying a fluid into a body cavity, said fluid discharge device having a longitudinal axis and comprising a container for storing the fluid to be dispensed and a compression pump having a suction inlet located within the container and a discharge tube extending along the longitudinal axis for transferring fluid from the pump to the nozzle, the housing assembly comprising a housing, a nozzle for insertion into a body cavity and finger operable means moveable transversely with respect to the longitudinal axis of the fluid discharge device to apply a force to the container to move the container along the longitudinal axis towards the nozzle so as to actuate the compression pump wherein a pre-load means is provided to prevent actuation of the compression pump until a pre-determined force is applied to the finger operable means.

According to a still further aspect of the present invention there is provided a kit of parts comprising a housing assembly as described above and a fluid discharge device receivable thereby. The fluid discharge device has a longitudinal axis and comprises a container for storing the fluid to be dispensed and a compression pump having a suction inlet located within the container and a discharge tube extending along the longitudinal axis for transferring fluid from the pump to the nozzle.

Suitably, the fluid discharge device herein comprises a pre-compression pump, such as a VP3, VP7 or modifications, model manufactured by Valois SA. Typically, such pre-compression pumps are typically used with a bottle (glass or plastic) container capable of holding 8-50 ml of a formulation. Each spray will typically deliver 50-100 µl of such a formulation and the device is therefore capable of providing at least 100 metered doses.

It is also envisaged that the housing assembly could be supplied as a separate item, into which a user or pharmacist later fits a suitable fluid discharge device.

BRIEF DESCRIPTION OF THE FIGURES

The invention will now be described further with reference to the accompanying drawing in which:—

FIG. 18 is a cross-section of a fluid dispensing device having an alternative mechanism to actuate the fluid discharge device to that shown in FIG. 1 and having a pre-load means according to a sixth embodiment of the invention;

FIG. 19 is a cross-section that is similar to that shown in FIG. 18 but showing an alternative pre-load means according to the sixth embodiment of the invention;

FIG. 22 is a cross-section of a fluid dispensing device having an alternative mechanism to actuate the fluid discharge device to that shown in FIG. 1 and having a pre-load means according to the second embodiment of the invention;

FIG. 23 is a side view in the direction of arrow 'T' on FIG. 22; and

FIG. 24 is cross-section of the area indicated by the arrow 'F' on FIG. 22.

DETAILED DESCRIPTION

Figure 1:
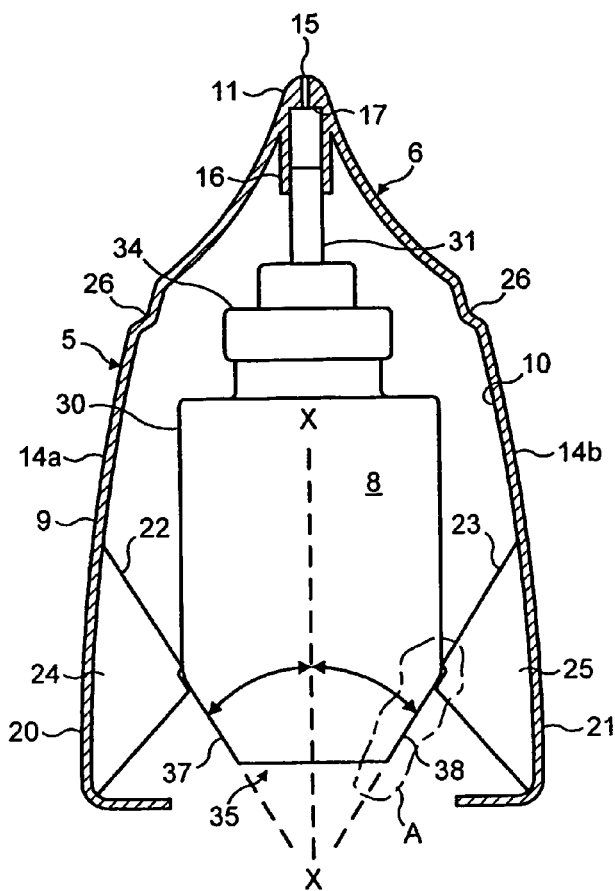
FIG. 1 is a cross-section through a fluid dispensing device including a fluid discharge device having a pre-load means according to a first embodiment of the invention in a ready for use state.
Figure 2A:
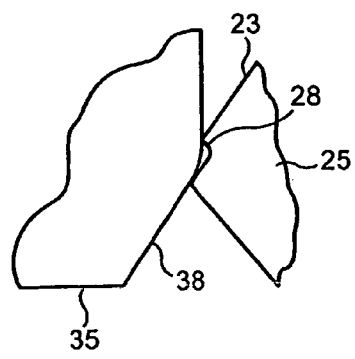
FIG. 2a is an enlarged view of the area indicated by the arrow 'A' on FIG. 1.
Figure 3:
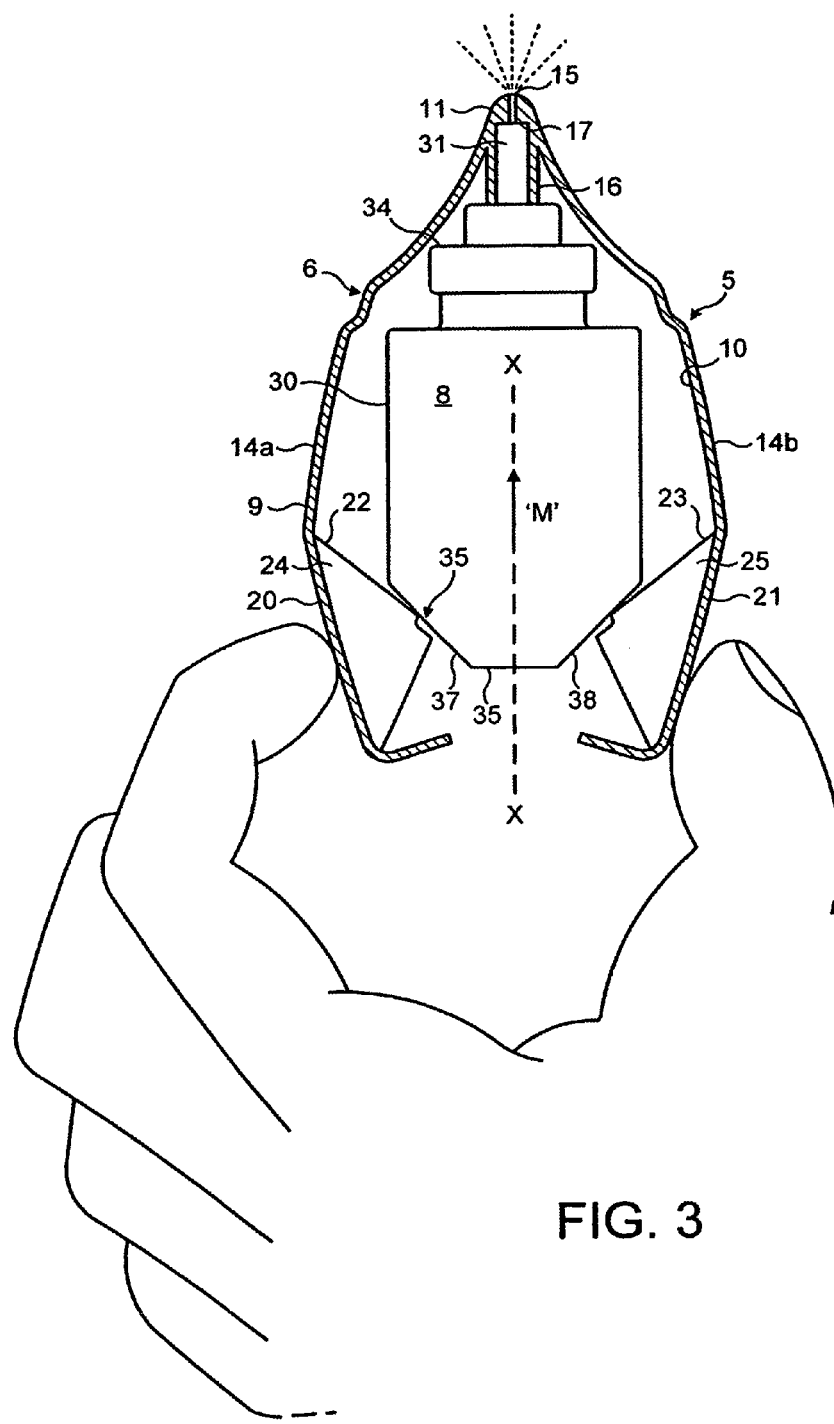
FIG. 3 is a cross-section similar to that of FIG. 1 but showing the fluid dispensing device in use.

With reference to FIGS. 1, 2a and 3 there is shown a fluid dispensing device 5 for spraying a fluid into a body cavity comprising a housing 9, a nozzle 11 for insertion into a body cavity, a fluid discharge device 8 moveably housed within the housing 9, the fluid discharge device 9 having a longitudinal axis and comprising a container 30 for storing the fluid to be dispensed and a compression pump having a suction inlet located within the container 30 and a discharge tube 31 extending along the longitudinal axis for transferring fluid from the compression pump to the nozzle 11 and finger operable means 20, 21 moveable transversely with respect to the longitudinal axis of the fluid discharge device to apply a force to the container 30 to move the container 30 along the longitudinal axis towards the nozzle 11 so as to actuate the compression pump and a pre-load means 28 to prevent actuation of the compression pump until a pre-determined force is applied to the finger operable means 20, 21.

The finger operable means is in the form of two opposing levers 20, 21 each of which is pivotally connected to part of the housing 9 and is arranged to act upon a base portion 35 of the container 30 so as to urge the container 30 towards the nozzle 11 when the two levers 20, 21 are squeezed together by a user.

The fluid dispensing device 5 comprises of a plastic moulded body 6 and the fluid discharge device 8 and further comprises of a protective end cap (not shown) having an inner surface for engagement with the body 6 to protect the dispensing nozzle 11.

The body 6 is made from a plastic material such as polypropylene and defines the housing 9 and the dispensing nozzle 11 so that the housing 9 and the nozzle 11 are made as a single plastic component.

The housing 9 defines a cavity 10 formed by a front wall, a rear wall and first and second end walls 14a, 14b. The dispensing nozzle 11 is connected to one end of the housing 9, extends away from the housing 9 and has an external tapering form.

The discharge outlet from the compression pump is in the form of the tubular delivery tube 31 and a tubular guide in the form of an outlet tube 16 is formed within the nozzle 11 to align and locate the delivery tube 31 correctly with respect to the nozzle 11.

An annular abutment 17 is formed at the end of the outlet tube 16. The annular abutment 17 defines the entry to an orifice 15 through which fluid can flow in use and is arranged for abutment with an end of the delivery tube 31.

The fluid discharge device 8 has a longitudinal axis X-X and each of the levers 20, 21 has an abutment surface 22, 23 arranged at an angle θ to the longitudinal axis X-X of the fluid discharge device 8 for abutment against the base portion 35 of the container so as to convert a force applied to the levers 20, 21 substantially transversely to the longitudinal axis X-X of the fluid discharge device 8 into a force along the longitudinal axis X-X of the fluid discharge device 8.

The nozzle 11 has a longitudinal axis that is aligned with the longitudinal axis X-X of the fluid discharge device 8. This has the advantage that when the compression pump is actuated the force applied to the tubular delivery tube 31 is along the axis of the tubular delivery tube 31 and no bending or deflection of the delivery tube 31 will occur due to the applied force.

At least part of the surface of the base portion 35 of the container 30 is inclined at an angle with respect to the longitudinal axis X-X of the fluid discharge device 8 so as to form an inclined surface, the or each inclined surface being arranged to be acted upon by the levers 20, 21 so as to convert a force applied to the levers 20, 21 substantially transversely to the longitudinal axis X-X of the fluid discharge device 8 into a force along the longitudinal axis X-X of the fluid discharge device 8.

Although in the disclosed embodiment both the levers and the container have surfaces inclined to the longitudinal axis of the fluid discharge device this need not be the case. Only the container or the levers need have an inclined surface or some other arrangement to apply the force from the levers to the container could be used.

The base portion 35 of the container 30 has two inclined surfaces 37, 38 each arranged for co-operation with a respective one of the levers 20, 21.

However it will be appreciated that the inclined surface of the base portion of the container could be a conical, frusto-conical or part spherical surface.

The inclined surface 37 is arranged to co-operate with the abutment surface 22 and the inclined surface 38 is arranged to co-operate with the abutment surface 23.

The abutment surface 22 is formed by an edge of a web 24 formed as part of the lever 20 and the abutment surface 23 is formed by an edge of a web 25 formed as part of the lever 21.

In the arrangement shown in FIG. 2A, the pre-loading means is interposed between the levers 20, 21 and the container and as shown is in the form of small step 28 formed near to the end of each abutment surface 22, 23. In the ready for use position this lies against a side of the container 30 at the juncture of the side of the container with the base portion 35. The purpose of this step 28 is to prevent the levers 20, 21 from moving the container 30 until more than a pre-determined force has been applied to the levers 20, 21.

The step 28 formed on each lever 20,21 must be ridden over by the container 30 before the compression pump can be actuated. The step 28 is over-ridden when the pre-determined force is applied to each lever 20,21 and once this pre-determined force is exceeded the pressure being applied to the levers 20, 21 is such that the container 30 is very rapidly moved towards the nozzle 11. This prevents the levers 20, 21 being slowly squeezed together which will not produce a uniform spray and if done very slowly will merely cause the fluid to dribble out of the nozzle 11.

Figure 2B:
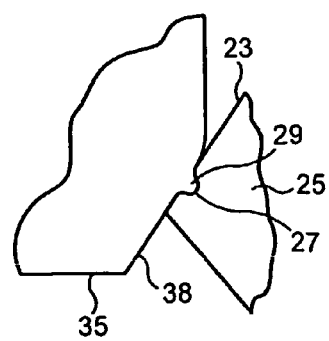
FIG. 2b is an enlarged view similar to that shown in FIG. 2a but showing an alternative pre-load means.

FIG. 2B shows an alternative arrangement in which the pre-load means comprises of a detent or protuberance 29 formed on the container 30 and complementary recess 27 formed on each lever 20,21. The size of the detent 29 is such that they are able to ride out of the recess 27 when the pre-determined force is applied to each lever 20, 21. It will be appreciated that in other alternatives, the recess could be formed in the container and the detent could be formed on the levers.

Each of the levers 20, 21 is pivotally connected to part of the housing 9 by a respective living hinge. In the embodiment shown each of the levers 20, 21 is pivotally connected to a respective one of the two side walls 14a, 14b by a respective living hinge 26 although other means of pivotal connection could be used.

The fluid discharge device 8 is in most respects conventional and will only be described briefly herein.

The fluid discharge device 8 has a hollow container 30 defining a reservoir containing several doses of the fluid to be dispensed and the compression pump that is attached to a neck 34 of the container 30.

The container 30 as shown is made from a translucent or transparent plastics material however it will be appreciate that it could be made from other translucent or transparent materials such as glass.

The compression pump includes a plunger (not shown) slidingly engaged within a pump casing that defines a chamber (not shown) sized to accommodate a single dose of fluid. The plunger is attached to the tubular delivery tube 31 that is arranged to extend from one end of the pump for co-operation with the outlet tube 16 of the dispensing nozzle 11. The plunger includes a piston (not shown) slidably supported in the chamber formed in the pump casing.

The fluid is discharged through a discharge channel defined by the tubular delivery tube 31 into the orifice 15 of the dispensing nozzle 11.

The size of chamber is such that it accommodates a single dose of fluid, the diameter of the chamber and piston combined with the stroke of the plunger being such that a full stroke of the plunger in the chamber will produce a change in volume equal to a single dose of fluid.

The pump casing is connected to the container 30 such that when the piston is moved by a return spring of the pump (not shown) into a start position a new dose of fluid is drawn into the cylinder via the suction inlet in the form of a pick-up tube from the container 30 ready for discharge.

Operation of the fluid dispensing device is as follows.

From the position shown in FIG. 1 in which the end portions of the abutment surfaces 22, 23 abut gently against the inclined surfaces 37, 38 of the container 30 and the container 30 is abutting with the steps 28 a user first grasps the fluid dispensing device 5 by the two levers 20, 21. Provided that only a light pressure is applied to the levers 20, 21 no fluid will be discharged and the user is able to manoeuvre the dispensing nozzle 11 of the fluid dispensing device 5 into the body orifice into which fluid is required to be dispensed. This is because of the presence of the pre-loading means formed in alternative embodiments, by the steps 28 of FIG. 2A or the detents/recesses 29, 27 arrangement of FIG. 2B.

If the user then squeezes the two levers 20, 21 together with increasing force the pre-determined force required to cause the container 30 to ride up over the steps 28 (or detents/recesses 29, 27) will be attained and the interaction of the abutment surfaces 22, 23 with the inclined surfaces 37, 38 will then cause the container 30 to be moved rapidly towards the nozzle 11 as indicated by the arrow 'M' on FIG. 3.

However, the abutment between the end of the delivery tube 31 and the annular abutment 17 will prevent movement of the delivery tube 31 in the same direction.

This effect of this is to cause the delivery tube 31 to push the plunger into the pump casing thereby moving the piston of the pump in the cylinder. This movement causes fluid to be expelled from the cylinder into the delivery tube 31. The fluid forced into the delivery tube is then transferred into the orifice 15 from where it is expelled as a fine spray into the body orifice.

Upon releasing the pressure applied to the levers 20, 21 the delivery tube 31 is urged out of the pump casing by the internal return spring and causes fluid to be drawn up the pick-up tube to re-fill the cylinder. The container 30 will then be allowed to move back into engagement with the steps 28 formed in the levers 20, 21 ready for the next actuation of the fluid dispensing device 5.

The actuating procedure can then be repeated until all of the fluid in the container has been used. However, only one or two doses of fluid are normally administered at a time.

When the container is empty a new fluid discharge device 8 is loaded into the housing 9 thereby restoring the fluid dispensing device 5 into a useable condition.

Figure 4:
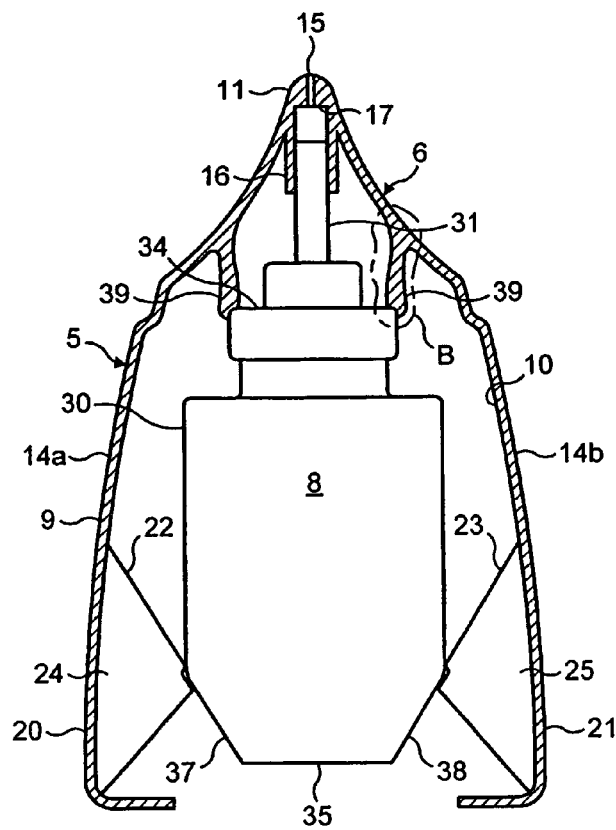
FIG. 4 is a cross-section similar to that shown in FIG. 1 but showing a pre-load means according to a second embodiment of the invention.
Figure 5:
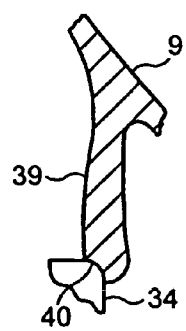
FIG. 5 is an enlarged view of the area indicated by the arrow 'B' on FIG. 4.

With reference to FIGS. 4 and 5 there is shown a fluid dispensing device that is in most respects identical to that previously described and for which the same reference numerals are used for like components.

The primary difference between the fluid dispensing means shown in FIGS. 1 to 3 and that shown in FIGS. 4 and 5 is that the fluid dispensing device 5 in FIGS. 4 and 5 uses a second embodiment of pre-load means in which the pre-load means 39, 40 is interposed between the housing 9 and the container 30.

The pre-load means comprises of two detents 39, 40 formed on the housing 9 for engagement with part of the container 30. The two detents 39, 40 are disengageable from the container 30 when the pre-determined force is applied to the finger operable means 20, 21 so as to allow the compression pump to be actuated.

Each of the detents is in the form of an arm 39, which extends downwardly from the housing 9 for engagement with a corner of the neck 34 of the container 30. A free end of each arm 39 has a step 40 formed therein, which prior to actuation is in abutting contact with the neck 34 of the container 30.

Operation of the fluid dispensing device is as follows.

From the position shown in FIG. 4 in which the end portions of the abutment surfaces 22, 23 abut gently against the inclined surfaces 37, 38 of the container 30 and the container 30 is abutting with the steps 40 a user first grasps the fluid dispensing device 5 by the two levers 20, 21. Provided that only a light pressure is applied to the levers 20, 21 no fluid will be discharged and the user is able to manoeuvre the dispensing nozzle 11 of the fluid dispensing device 5 into the body orifice into which fluid is required to be dispensed. This is because of the presence of the pre-loading means formed by the steps 40 and the arms 39 which prevent movement of the container towards the nozzle.

If the user then squeezes the two levers 20, 21 together with increasing force the arms 39 will begin to bow outwardly until when the pre-determined force is reached the neck 34 of the container 30 is able to disengaged itself from the steps 40 and the interaction of the abutment surfaces 22, 23 with the inclined surfaces 37, 38 will then cause the container 30 to be moved rapidly towards the nozzle 11.

However, as previously described the abutment between the end of the delivery tube 31 and the annular abutment 17 will prevent movement of the delivery tube 31 in the same direction thereby causing the compression pump to be actuated as the delivery tube 31 is pushed into the container 30. This movement causes fluid to be expelled from the container 30 into the delivery tube 31 and then into the orifice 15 from where it is expelled as a fine spray into the body orifice.

Upon releasing the pressure applied to the levers 20, 21 the delivery tube 31 is urged out of the container 30 causing fluid to re-fill the pump. The container 30 will then move back into engagement with the steps 40 formed in the arms 39 ready for the next actuation of the fluid dispensing device 5.

The actuating procedure can then be repeated until all of the fluid in the container has been used. However, only one or two dose volumes of fluid are normally administered at a time.

Figure 6:
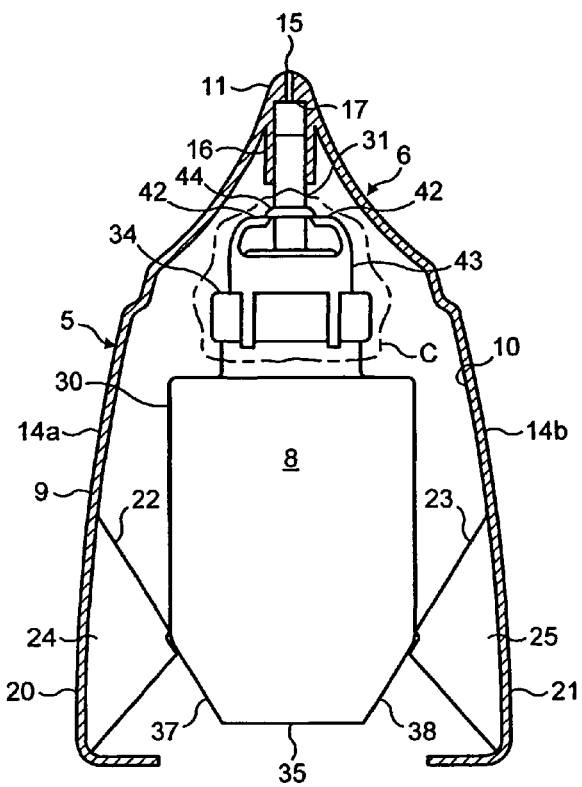
FIG. 6 is a cross-section similar to that shown in FIG. 1 but showing a pre-load means according to a third embodiment of the invention.
Figure 7:
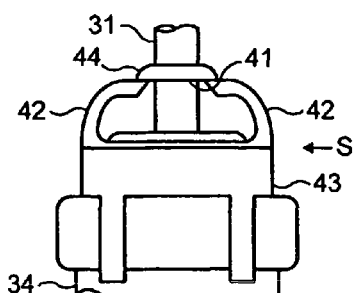
FIG. 7 is an enlarged view of the area indicated by the arrow 'C' on FIG. 6.
Figure 8:
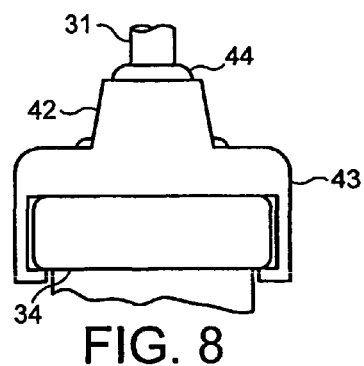
FIG. 8 is a side view in the direction of arrow 'S' on FIG. 7.

With reference to FIGS. 6 to 8 there is shown a fluid dispensing device that is in most respects identical to that previously described with respect to FIGS. 1 to 3 and for which the same reference numerals are used for like components.

The primary difference between the fluid dispensing means shown in FIGS. 1 to 3 and that shown in FIGS. 6 to 8 is that the fluid dispensing device 5 in FIGS. 6 to 8 uses a third embodiment of pre-load means in which the pre-load means 41, 42, 43 is interposed between the container 30 and the discharge tube 31.

This embodiment has the advantage that it can be used irrespective of the mechanism used to actuate the pump.

The pre-load means comprises of a step 41 formed on the discharge tube 31 and two latching members in the form of arms 42 attached by a collar 43 to the neck 34 of the container 30. The step 41 is formed by a rib 44 extending circumferentially around the discharge tube 31 and positioned such that when the pump is actuated the rib 44 does not prevent travel of the discharge tube 31 into the container 30.

The arrangement is such that, when the pre-determined force is applied to the finger operable means in the form of the levers 20, 21, the latching members or arms 42 are able to ride over the step 41 so as to allow the compression pump to be actuated but when a force below the pre-determined force is applied the interengagement of the arms 42 with the step 41 prevents the discharge tube 31 from moving into the container 30.

Operation of the fluid dispensing device is as previously described and provided that only a light pressure is applied to the levers 20, 21 no fluid will be discharged and the user is able to manoeuvre the dispensing nozzle 11 of the fluid dispensing device 5 into the body orifice into which fluid is required to be dispensed. This is because of the presence of the pre-loading means formed by the step 41 and the arms 42 which prevent movement of the container 30 towards the nozzle 11.

If the user then squeezes the two levers 20, 21 together with increasing force the arms 42 will begin to bow until when the pre-determined force is reached the arms 42 are able to disengage themselves from the step 41 and the interaction of the abutment surfaces 22, 23 with the inclined surfaces 37, 38 will then cause the container 30 to be moved rapidly towards the nozzle 11.

This movement causes fluid to be expelled from the container 30 into the delivery tube 31 and then into the orifice 15 from where it is expelled as a fine spray into the body orifice.

Upon releasing the pressure applied to the levers 20, 21 the delivery tube 31 is urged out of the container 30 causing fluid to re-fill the pump. The container 30 will then move back allowing the arms 42 to re-engage with the step 41 ready for the next actuation of the fluid dispensing device 5.

The actuating procedure can then be repeated until all of the fluid in the container has been used. However, only one or two doses of fluid are normally administered at a time.

It will be appreciated that alternatively, the pre-load means may comprise of a recess formed on the discharge tube 31 and at least one latching member or arm attached to the container 30, the arrangement being such that, when the pre-determined force is applied to the finger operable means in the form of the levers 20, 21 the or each latching member is able to ride out of the recess so as to allow the compression pump to be actuated.

Figure 9:
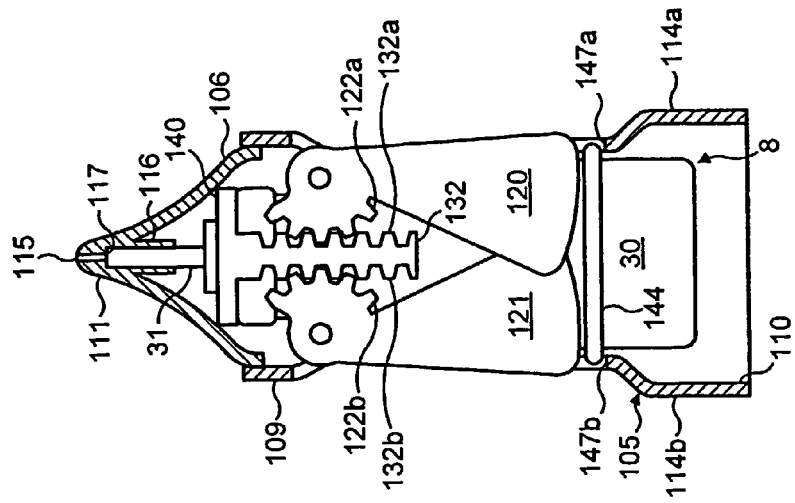
FIG. 9 is a cross-section of a fluid dispensing device having an alternative mechanism to actuate the fluid discharge device to that shown in FIG. 1 and having a pre-load means according to the second embodiment of the invention.
Figure 10:
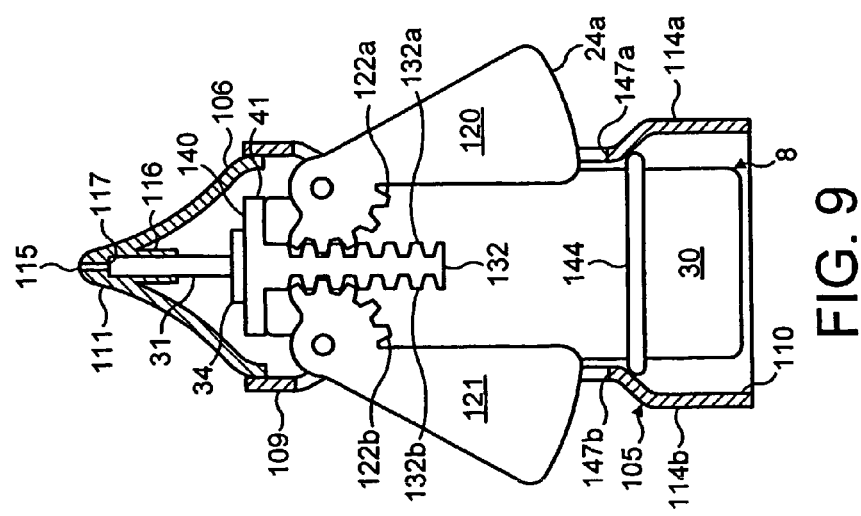
FIG. 10 is a cross-section as shown in FIG. 9 but showing the mechanism used to actuate the fluid discharge device in an actuated position.

With reference to FIGS. 9 and 10 there is shown a fluid dispensing device 105 which is in many respects similar to that previously described but instead of direct actuation of the fluid discharge device by the levers, the finger operable means in the form of two lever 120, 121 are used to apply a force to an actuating means 122a, 122b; 132, 132a, 132b used to move a container 30 towards a nozzle 111 so as to actuate the pump. For similar parts the same reference numerals will be used to those previously used in respect of FIGS. 1 to 3

The actuating means 122a, 122b, 132, 132a, 132b is connected to a neck 34 of the container 30.

The fluid dispensing device 105 for spraying a fluid into a body cavity comprises a housing 9, a nozzle 11 for insertion into a body cavity and a fluid discharge device 8 moveably housed within the housing 9. The fluid discharge device 8 comprises of a container 30 for storing the fluid to be dispensed and a compression pump having a suction inlet located within the container 30 and a discharge outlet 31 at one end of the container 30 for transferring fluid from the pump to the nozzle 11.

A finger operable means in the form of the two levers 120, 121 is provided to apply a force to the container 30 to move the container 30 towards the nozzle 11 so as to actuate the pump.

The two opposing levers 120, 121 are pivotally supported within the housing 9 and are driveably connected to the container 30 by means of the actuating means so as to urge the container 30 towards the nozzle 11 when each lever 20, 21 is rotated by a user and in practice the two levers 120, 121 are squeezed together by a user. That is to say, squeezing the two levers 120, 121 together causes the container 30 to be moved towards the nozzle 11.

In more detail, the fluid dispensing device 5 comprises of a housing assembly and the fluid discharge device 8. The housing assembly comprises of the housing 9 for moveably supporting the fluid discharge device 8, a body 6 having the nozzle 11 extending therefrom and the two levers 120, 121 pivotally supported within the housing 9.

The body 6 and the nozzle 11 are made as a single part from a plastic material such as polypropylene and the body 6 is adapted at a lower end for engagement with an upper end of the housing 9. The body 6 and the housing 9 are fixed together by any suitable means.

The housing 9 defines a cavity 10 formed by a front wall, a rear wall and first and second end walls 14a, 14b.

The discharge outlet from the pump is in the form of a tubular delivery tube 31 and a tubular guide in the form of an outlet tube 16 is formed within the nozzle 11 to align and locate the delivery tube 31 correctly with respect to the nozzle 11.

An annular abutment 17 is formed at the end of the outlet tube 16. The annular abutment 17 defines the entry to an orifice 15 through which fluid can flow in use and is arranged for abutment with an end of the delivery tube 31.

The fluid discharge device 8 has a longitudinal axis coincident with a longitudinal axis of the container 30 and a longitudinal axis of the tubular delivery tube 31. The nozzle 11 has a longitudinal axis which is aligned with the longitudinal axis of the fluid discharge device 8 so that when the pump is actuated the force applied to the tubular delivery tube 31 is along the longitudinal axis of the tubular delivery tube 31 and no bending or deflection of the delivery tube 31 will occur due to the applied force.

Each of the first and second levers 120, 121 is driveably connected to the container 30 near to said one end of the container 30 where the container terminates in a neck 34.

To form the driveable connection each of the first and second levers 120,121 has a pair of toothed portions 122a, 122b for engagement with a respective toothed rack 132 attached to the container 30 and in particular to the neck portion 34 of the container 30. Each of the racks 132 is arranged so as to extend parallel to the longitudinal axis of the container 30.

Each of toothed racks 132 has two sets of opposed teeth, a first set of teeth 132a for engagement with the first lever 120 and a second set of teeth 132b for engagement with the second lever 121.

The neck portion 34 of the container 30 has a cylindrical outer surface and the two toothed racks 132 are arranged on opposite sides of the neck portion 34 so that the two toothed racks 132 are arranged diametrically opposite with respect to the neck portion 34.

Each of the toothed racks 132 is connected to a collar 140 used to attach the toothed racks 132 to the neck portion 34 of the container 30.

It will be appreciated that the levers 120, 121 can be pivotally attached to the housing 9 in any convenient manner or that each lever 120, 121 could be pivotally supported within the housing 9 by a pivotal connection between each lever 120, 121 and the body member 6.

The fluid discharge device 8 is as has previously been described and will not be described again other than to mention that actuation of the pump occurs when the discharge tube 31 is pushed into the container 30.

The fluid dispensing device 105 is fitted with a pre-load means according to the second embodiment of the invention, that is to say, the pre-load means 144 is interposed between the housing 9 and the container 30.

The pre-load means comprises of a detent in the form of a circumferentially extending rib 144 formed on the container 30 for engagement with part of the housing 9. The rib 144 is arranged for engagement with two inwardly extending fingers 147a, 147b formed in the side walls 14a, 14b of the housing 9. Each of the fingers 147a, 147b is attached to the respective side wall 14a, 14b be a living hinge such that movement of the fingers 147a, 147b towards the nozzle is prevented but pivoting of the fingers 147a, 147b relative to the housing 9 is possible when they are urged away from the nozzle 11. This provides a resistance to passage of the rib 144 if the container 30 is moved towards the nozzle 11 but offers little to resistance to passage of the rib 144 if the container is moving away from the nozzle 11.

Therefore, the detent or rib 144 is disengageable from the housing 9 or more specifically the fingers 147a, 147b when a pre-determined force is applied to the finger operable means 120, 121 so as to allow the compression pump to be actuated.

Operation of the fluid discharge device 105 is as follows.

First, a user must grasp the fluid dispensing device 105 by the two levers 120, 121, provided that only a light pressure is applied to the levers 120, 121 no fluid will be discharged due to the interaction between the rib 144 and the two fingers 147a, 147b and the user is able to manoeuvre the dispensing nozzle 11 of the fluid dispensing device 5 into the body orifice into which fluid is required to be dispensed. If the user then squeezes the two levers 120, 121 together with increasing force eventually a pre-determined force will be reached at which point the rib 144 is able to disengage with the housing 9 by riding over the fingers 147a, 147b and the interaction of the toothed portions 22a, 22b with the racks 32 will then cause the container 30 to be moved rapidly towards the nozzle 11.

However, because the end of the delivery tube 31 is in abutting contact with the annular abutment 17, the delivery tube 31 cannot move in the same direction. The effect of this is to cause the delivery tube 31 to be pushed into the container causing fluid to be expelled from the delivery tube 31 into the orifice 15 from where it is expelled as a fine spray into the body orifice.

At the end of the delivery stage when the fluid discharge device has been discharged the two levers 120, 121 have been rotated so that they lie close to or flush with the side walls 14a, 14b as shown in FIG. 10.

Upon releasing the pressure applied to the levers 120, 121 the delivery tube 31 is urged out of the pump casing by an internal return spring and causes fluid to be drawn up to re-fill the pump.

The actuating procedure can then be repeated until all of the fluid in the container has been used. However, only one or two volumes of fluid are normally administered at a time.

When the container is empty a new fluid discharge device 8 is loaded into the housing 9 thereby restoring the fluid dispensing device 105 into a useable condition.

Figure 11:
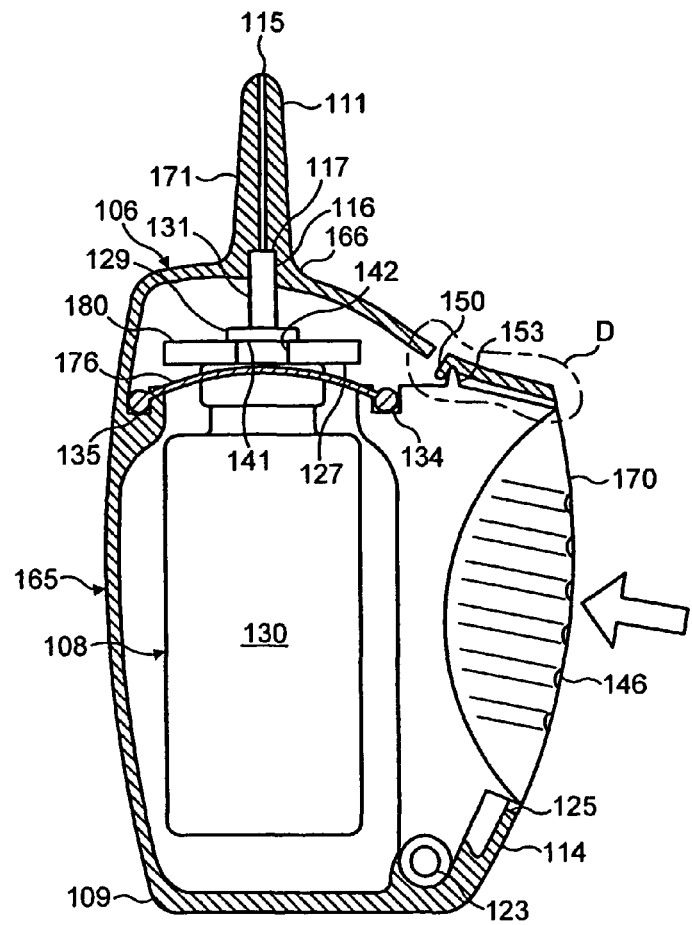
FIG. 11 is a cross-section of a fluid dispensing device having an alternative mechanism to actuate the fluid discharge device to that shown in FIG. 1 and having a pre-load means according to a fourth embodiment of the invention.
Figure 12:
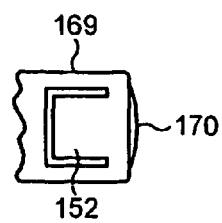
FIG. 12 is a plan view of the area indicated by the arrow 'D' on FIG. 11.

With reference to FIGS. 11 and 12 there is shown a fluid dispensing device 165 which is in many respects similar to that shown in FIGS. 1 to 3 but in which a single lever 170 is used to apply a force to an actuating means 176 used to move a container 130 towards a nozzle 111 and actuate a compression pump. The lever 170 is pivotally supported at a lower end within a housing 109 and the actuating means 176 is connected to a neck 129 of the container 130 by a collar 140.

The fluid dispensing device 165 is fitted with a fourth embodiment of a pre-load means in which the pre-load means 150, 152, 153 is interposed between the housing 109 and the lever 170.

The pre-load means comprises of a detent in the form of a tooth 150 formed on the housing 109 for engagement with the lever 170. The tooth 150 is formed at the end of an arm 152 formed as an integral part of the housing 109 and the lever 170 has a complementary rib 153 formed thereon for engagement with the tooth 150.

The detent or tooth 150 is disengageable from the rib 153 on the lever 170 when a pre-determined force is applied to the lever 170 so as to allow the compression pump to be actuated.

In more detail the fluid dispensing device 165 comprises of a body structure including the housing 109, the nozzle 111 extending out from an upper end of the housing 109 for insertion into a body cavity and a fluid discharge device 108 moveably housed within the housing 109.

The fluid discharge device 108 comprises of the container 130 for storing the fluid to be dispensed and the compression pump having a suction inlet located within the container 130 and a discharge outlet 131 for transferring fluid from the pump to the nozzle 111.

The lever 170 is pivotally supported at a lower end within the housing 109 and the actuating means is connected to the neck 129 of the container 130 by a collar 140 engaged with the neck 129 of the container 130.

The body structure comprises of a two-part plastic housing 109 and a plastic body member 106 both of which are moulded from a suitable plastic material such as polypropylene. The nozzle 111 is formed as an integral part of the body member 106 and the body member 106 is fastened to the housing 109 so that the nozzle 111 projects from the upper end of the housing 109.

The housing 109 has an aperture formed in a side wall 114 from which, in use, a part of the lever 170 projects. The part of the lever 170 that projects from the aperture is a ribbed finger grip 146.

The discharge outlet from the pump is in the form of a tubular delivery tube 131 and a tubular guide in the form of an outlet tube 116 is formed within the nozzle 111 to align and locate the delivery tube 131 correctly with respect to the nozzle 111.

An annular abutment 117 is formed at the end of the outlet tube 116. The annular abutment 117 defines the entry to an orifice 115 through which fluid can flow in use and is arranged for abutment with an end of the delivery tube 131.

The fluid discharge device 108 is in most respects conventional and is as previously described herein.

The collar 140 is connected to the neck 129 of the container 130 by a snap connection in which the neck 129 has a groove 141 into which the collar 140 is snap fitted. The collar 140 has a slit 142 in one side that allows it to be pushed onto the neck 129 and engage with the groove 141.

The actuating means is a resilient flexible member in the form of a leaf spring 176 connected to an upper end of the lever 170 so as to hold the resilient flexible member 176 in an upwardly bowed state. However, it will be appreciated that more than one resilient flexible member could be used if required.

The lower end of the lever 170 is pivotally connected to the housing 109 by means of a pivot pin 123.

The resilient flexible member 176 is operably connected to the neck 129 of the container 130 by abutment of an upper surface of the resilient flexible member 176 against a lower surface 127 of the collar 140, which is attached to the neck 129 of the container 130.

A stop means 125 is provided to limit rotational movement of the lever 170 away from the container 130 so as to maintain the resilient flexible member 176 in a bowed state. The stop means 125 takes the form of one edge of the aperture through which the lever 170 projects.

The resilient flexible member 176 is connected at one end to the upper end of the lever 170 by engagement with a groove 134 formed in the lever 170 and is connected at an opposite end to part of the body structure of the fluid dispensing device 165 in the form of the housing 109 which has a groove 135 formed therein with which the resilient flexible member 124 is engaged.

It will be appreciated that if removed from the fluid dispensing device 165 the resilient flexible member will return to a flat planar shape as it undergoes no plastic deformation during use but only elastic deformation.

The stop 125 is positioned such that when the lever 120 is displaced fully from the container 130 so as to rest against the stop 125 the linear distance between the upper end of the lever 120 and the position of connection of the resilient flexible member 176 to the housing 109 is less than the un-bowed length of the resilient flexible member 176. This ensures that the flexible member never returns to a flat shape. This is important because the resilient flexible member must be bowed upwardly to function correctly and if it were to be fully released there is a possibility that upon re-applying a load to it would bow downwardly.

When the lever 120 is moved towards the container 130 so as to cause the container 130 to be moved towards the nozzle 111, the radius of curvature of the bowed resilient flexible member 176 is reduced and the collar 140 is moved upwardly thereby causing actuation of the pump.

Operation of the fluid dispensing device 165 is as follows.

After inserting a fluid discharge device 108 into the housing 109 the fluid dispensing device is ready for use and the lever 170 will be resting against the end stop 125.

To use the fluid dispensing device 165 a user must first grasp the fluid dispensing device 165 so that contact is made with the lever 170 and in particular with the ribbed finger grip 146.

Provided that only a light pressure is applied to the lever 170 no fluid will be discharged and the user is able to manoeuvre the dispensing nozzle 111 of the fluid dispensing device 165 into a body orifice such as a nasal cavity into which fluid is required to be dispensed. This is because of the presence of the pre-load means and in particular because the tooth 150 is abutting with the rib 153.

If the user then exerts more force upon the lever 170 the arm 152 will begin to bend and when the force applied to the lever 170 reaches a predetermined magnitude the tooth 150 is able to ride over or become detached from the rib 153 allow the lever 170 to move freely and the interaction of the resilient flexible member 176 upon the collar 140 will then cause the container 130 to be moved rapidly towards the nozzle 111.

This causes the delivery tube 131 to be pushed into the container thereby actuating the pump.

Upon releasing the pressure applied to the lever 170, the resilient flexible member 176 will try to assume is least deformed state and so will urge the lever 170 back upon its stop 125 as soon as the force is removed from the lever 170 allowing the tooth 150 to re-engage with the rib 153.

The actuating procedure can then be repeated until all of the fluid in the container has been used. However, only one or two doses of fluid are normally administered at a time.

When the container 130 is empty a new fluid discharge device 108 is loaded into the body member 106 thereby restoring the fluid dispensing device 165 into a useable condition.

Figure 13:
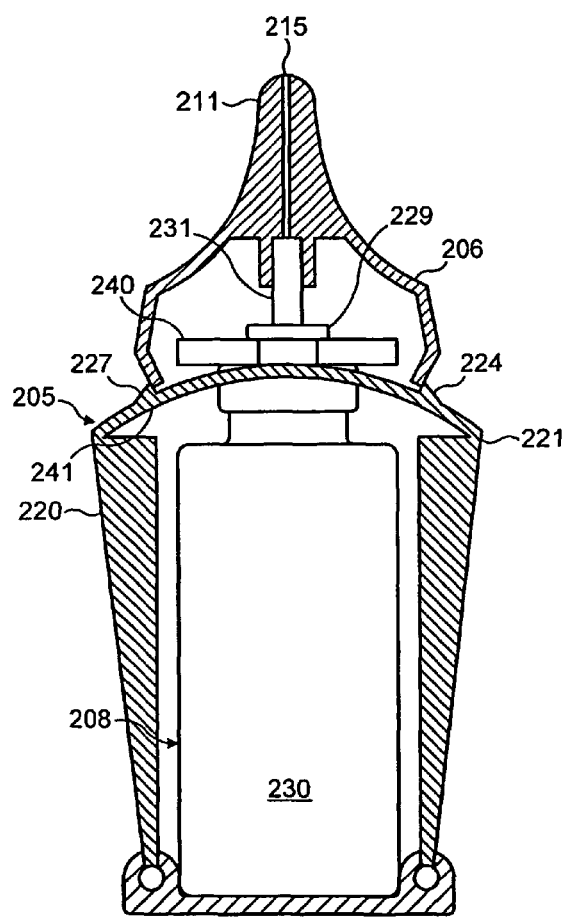
FIG. 13 is a cross-section of a fluid dispensing device having an alternative mechanism to actuate the fluid discharge device to that shown in FIG. 1 and having a pre-load means according to a fifth embodiment of the invention.
Figure 15:
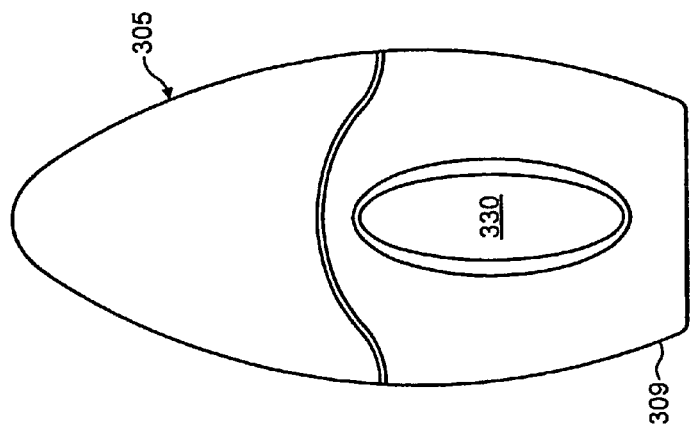
FIG. 15 is a front view of the fluid dispensing device shown in FIG. 14 with an end cap in place.
Figure 14:
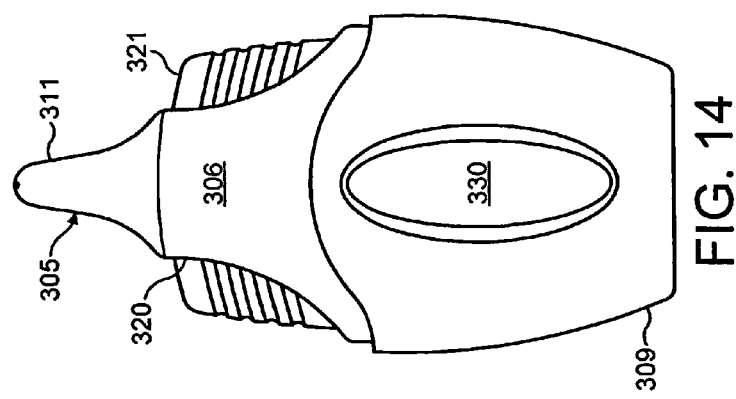
FIG. 14 is a front view of a fluid dispensing device having an alternative mechanism to actuate the fluid discharge device to that shown in FIG. 1 and having a pre-load means according to the fourth embodiment of the invention with an end cap removed.
Figure 16:
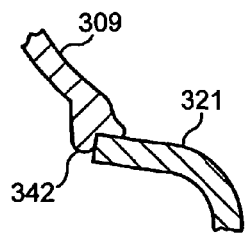
FIG. 16 is an enlarged cross-section of the area indicated by the arrow 'E' on FIG. 17.
Figure 17:
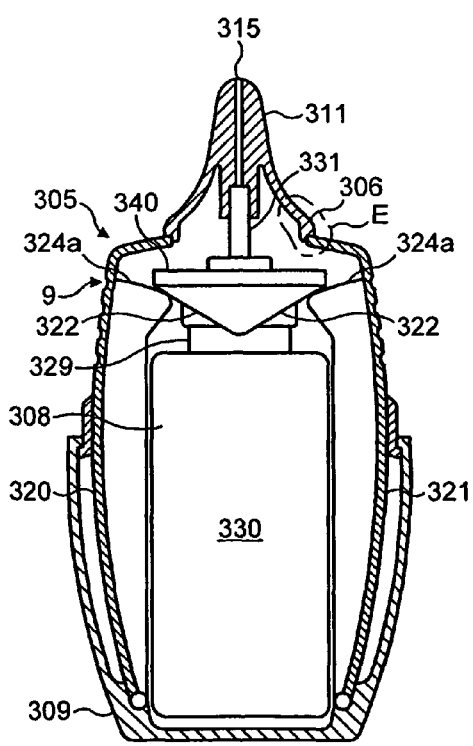
FIG. 17 is a cross-section of a fluid dispensing device shown in FIG. 14.

With particular reference to FIG. 13 there is shown a fluid dispensing device 205 which is in many respects similar to that described with respect to FIG. 11 but in which two levers 220, 221 pivotally supported at their lower ends are used to move a container 230 forming part of a discharge device 208 housed within a housing 206 by means of an actuating means in the form of a flexible member 241 which as shown is formed as a single part with the two levers 220, 221 but all three parts could be made as separate components.

The flexible member 242 is arranged to act against a collar 240 connected to a neck 229 of the container 230 so that when the two levers are squeezed together the flexible member 241 urges the container towards a nozzle 211 extending from one end of the housing 206. The movement of the container 230 towards the nozzle 211 causes relative movement between the container 230 and a discharge tube 231 connected to a pump housed within the container 230 thereby actuating the pump and causing fluid to be urged out through the discharge tube 231 into an orifice 215 formed in the nozzle 211 from whence it is dispensed as fine spray.

The fluid dispensing device 205 is fitted with a fifth embodiment of a pre-load means in which the pre-load means is interposed between the actuating means 241 and the housing 206.

The pre-load means comprises of two detents 224, 227 formed on part of the actuating means and in this case on an upper surface of the flexible member 241 for engagement with part of the housing. As can be seen, each of the detents 224, 227 is located such that when the levers 220, 221 are in a rest position they abut lightly against an adjacent outer surface of the housing 206.

When a small force is applied to the two levers 220, 221 the pump is not actuated because the detents 224, 227 prevent the flexible member from moving but when a force of a predetermined magnitude is applied to the levers 220, 221 it is sufficient to cause the detents 224, 227 to disengage from the housing so as to allow the compression pump to be actuated. Because of the presence of the detents 224, 227 it is ensured that the container 230 is not moved until sufficient force is applied to the levers 220, 221 to cause rapid movement of the container 230 towards the nozzle 211 and guarantee that an effective spray is produced.

It will be appreciated that alternatively, the pre-load means could comprise of at least one detent formed on part of the housing for engagement with a complementary recess formed on part of the actuating means. In which case, each detent would be disengageable from its respective recess when the pre-determined force is applied to each lever so as to allow the compression pump to be actuated.

With reference to FIGS. 14 to 17 there is shown a fluid dispensing device 305 that is in many respects similar to those previously described.

The fluid dispensing device 305 comprises of a body 306 forming a nozzle 311 and a housing 309. A fluid discharge device 308 is housed within the housing 309. The fluid discharge device 308 comprises of a container 330 in which is fitted a compression pump (not shown) and a discharge tube 331 extending from one end of the container 330 for abutment against the nozzle 311. When the discharge tube 331 is moved into the container 330 the pump is actuated and fluid is urged out of the discharge tube 331 into an orifice 315 in the nozzle from whence it is emitted as a fine spray.

There is provided a finger operable means in the form of two opposing levers 320, 321 each of which is pivotally supported near a lower end of the housing 309 and is arranged to act upon an actuating means 322 so as to urge the container 330 towards the nozzle 311 when the two levers 320, 321 are squeezed together.

The actuating means is in the form of two inclined ramps 322 each of which is arranged to cooperate with a complementary inclined surface 324a formed on a respective one of the two levers 320, 321. The two ramps 322 are connected to the container 330 by means of a collar 340 that is engaged with a neck 329 of the container.

Movement of the two levers 320, 321 towards each other causes the inclined surfaces 324a to ride up the ramps 322 thereby urging the container towards the nozzle 311.

The fluid dispensing device 305 is fitted with a pre-load means interposed between the housing 309 and the levers 320, 321.

The pre-load means comprises of a detent or step 342 formed on each side of the housing 309 for engagement with an end face of each lever 320, 321.

Movement of the levers 320, 321 is prevented by their engagement with the steps 342 until a pre-determined force is applied to them at which point the force applied is sufficient to cause the ends of the levers 320, 321 to ride out of the steps 342 and permit free movement of the levers 320, 321 towards the container 330 thereby causing actuation of the pump. In this way it is guaranteed that the pump will not be actuated until sufficient force is being applied to cause a rapid movement of the discharge tube 331 into the container 330.

With reference to FIG. 18 there is shown a fluid dispensing device 405 that is in many respects similar to that previously described with reference to FIGS. 14 to 17 but in which the pre-load means is interposed between each lever 420, 421 and the respective actuating means 422.

The fluid dispensing device 405 comprises of a body 406 forming a nozzle 411 and a housing 409. A fluid discharge device 408 is housed within the housing 409. The fluid discharge device 408 comprises of a container 430 in which is fitted a compression pump (not shown) and a discharge tube 431 extending from one end of the container 430 for abutment against the nozzle 411. When the discharge tube 431 is moved into the container 430 the pump is actuated and fluid is urged out of the discharge tube 431 into an orifice 415 in the nozzle from whence it is emitted as a fine spray.

There is provided a finger operable means in the form of the two opposing levers 420, 421 each of which is pivotally supported near a lower end of the housing 409 by being connected together by a flexible strap 423 and is arranged to act upon the actuating means 422 so as to urge the container 430 towards the nozzle 411 when the two levers 420, 421 are squeezed together.

The actuating means is in the form of two inclined ramps 422 each of which is arranged to cooperate with a complementary curved surface formed on a respective one of the two levers 420, 421. The two ramps 422 are connected to the container 430 by means of a collar 440, which is engaged with a neck 429 of the container 430.

Movement of the two levers 420, 421 towards each other causes the curved portions of the levers 420, 421 to ride up the ramps 422 thereby urging the container 430 towards the nozzle 411.

The fluid dispensing device 405 is fitted with a pre-load means interposed between the actuating device 422 and the levers 420, 421.

The pre-load means comprises of a detent 424a formed on each actuating means in the form of an inclined ramp 422 for engagement with a recess 446 formed in each lever 420, 421.

Each of the detents 424a is disengageable from its respective complementary recess 446 when a pre-determined force is applied to the respective lever 420, 421 so as to allow the compression pump to be actuated.

Operation of the fluid dispensing device is as previously described when a user grasps the two levers 420, 421 with less than the pre-determined force movement of the levers 420, 421 is prevented by the engagement of the detents 424a with the recesses 446 but as soon as a force equal to or greater than the pre-determined force is applied to the levers 420, 421 then the detents 424a are able to disengage or ride out of the recesses 446 and the two levers 420, 421 will move rapidly together thereby actuating the compression pump.

This ensures that the pump is only actuated when sufficient force is being applied to guarantee the production of an effective spray.

It will be appreciated that the pre-load means could alternatively comprises of at least one detent formed on each lever for engagement with a respective recess formed on part of the actuating means. In which case, each detent would be disengageable from its respective complementary recess when the pre-determined force is applied to the lever so as to allow the compression pump to be actuated.

With reference to FIG. 19 there is shown a fluid dispensing device 405 that is in many respects similar to that previously described with reference to FIG. 18 but in which an alternative form of pre-load means is interposed between each lever 420, 421 and the respective actuating means 422. The same reference numerals are used for like parts and the construction of the fluid dispensing device 405 will not be described further except so far as it relates to the pre-load means.

Figure 19A:
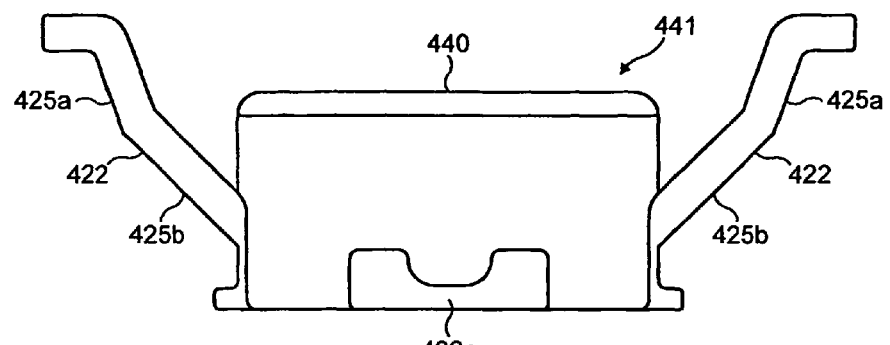
FIG. 19A is an enlarged side view of the collar occupying area indicated by the arrow 'J' on FIG. 19.
Figure 19B:
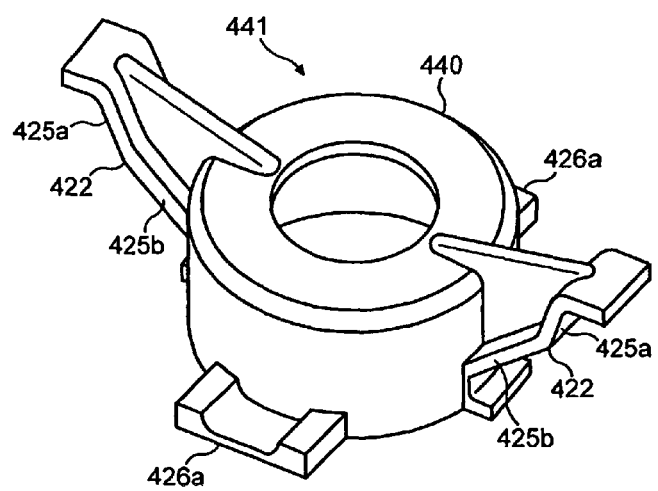
FIG. 19B is an enlarged perspective view of the collar of FIG. 19B.

The features of the actuating device 422 may be better understood having regard to FIGS. 19A and 19B, which show side and perspective views thereof.

The pre-load means comprises of an actuating device 441 having a collar 440 for receipt by neck 429 of the container 430. The actuating device 441 is provided on opposing sides with ramps 422, each having a variable mechanical ratio such that until a pre-determined force is applied to each lever 420, 421 no significant force is transferred to the container 430.

This is achieved by having a first portion 425a of each ramp 422 inclined at a lesser angle (e.g. approx 20°) to a longitudinal (i.e. vertical, as shown) axis of the fluid discharge device 408 than is the remaining length 425b (e.g. angle approx. 45°) of each ramp 422. Therefore when a force is initially applied to each lever 420, 421 it is applied substantially normal to the longitudinal axis of the fluid discharge device 408 and virtually no force is converted into a force along the longitudinal axis of the fluid discharge device 408 and so the static friction between the first portion 425a of each ramp 422 and the cooperating lever 420, 421 is sufficient to maintain the levers 420, 421 stationary. However, when a pre-determined load is applied to each lever 420, 421 the static friction is overcome and each lever 420, 421 is able to start moving along the first portion 425a of the cooperating ramp 422. When each lever 420, 421 reaches the end of the first portion 425a, the change in inclination of the surface with which the lever 420, 421 is cooperating in combination with the magnitude of the force being applied ensures that each lever 420, 421 suddenly slides rapidly along the second portion 425b of the cooperating ramp 422 causing the container 430 to be moved rapidly towards the nozzle 411 to actuate the compression pump.

This ensures that the pump is only actuated when sufficient force is being applied to guarantee the production of an effective spray.

As visible in FIGS. 19A and 19B, the actuating device 441 is also provided on opposing sides of the collar 440 with guide rails 426a, each perpendicularly arranged with respective to both ramps 422. The guide rails 426a interact with mating guides (not visible) on the housing 409 to ensure uniform longitudinal movement of the container 430 during actuation.

Figure 21:
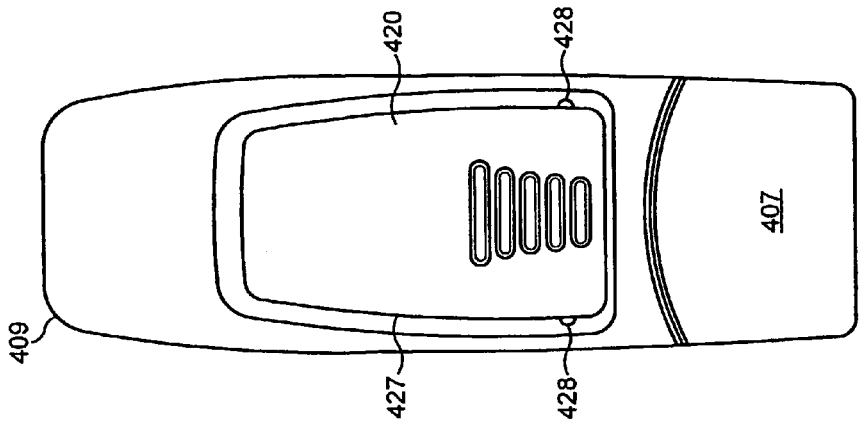
FIG. 21 is a side view in the direction of the arrow 'P' on FIG. 20.
Figure 20:
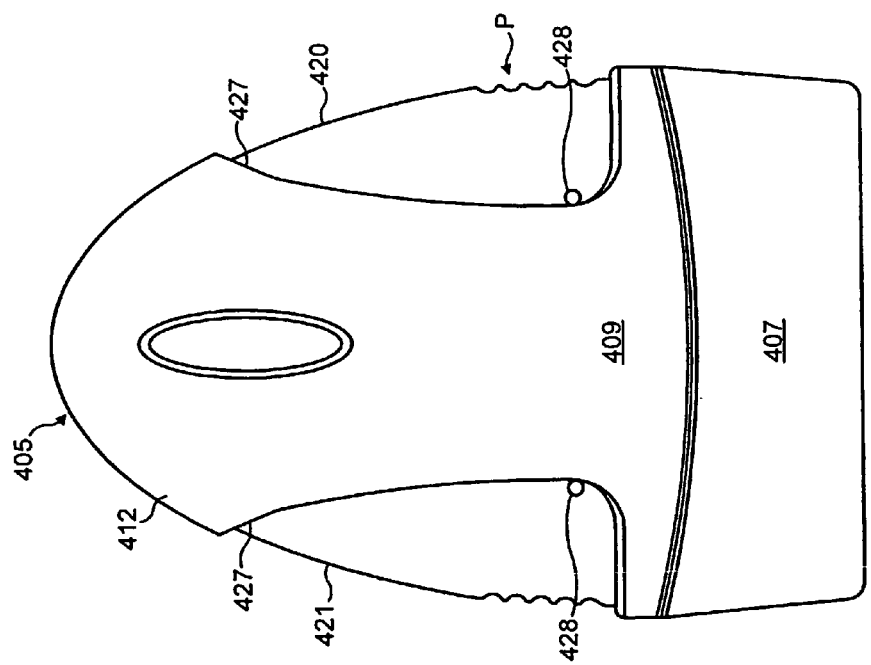
FIG. 20 is a front view of the fluid dispensing device shown in FIGS. 18 and 19 but showing the use of a pre-load means according to the fourth embodiment of the invention.

With reference to FIGS. 20 and 21 there is shown a fluid dispensing means that is in most respects identical to that previously described with respect to FIGS. 18 and 19 and for which the same reference numerals are used for identical parts. The only difference between the fluid dispensing device 405 shown in FIGS. 20 and 21 and those shown in FIGS. 18 and 19 is the arrangement of the pre-load means, which in this case is interposed between each of the levers 420, 421 and the housing 409. In addition, an end cap 407 is shown fitted in FIGS. 20 and 21.

The pre-load means comprises of two detents or protrusions 428 formed on each of the levers 420, 421 for engagement with a bevelled surface 427 formed around the periphery of an aperture in the housing 409 through the respective lever 420, 421 projects.

When a light force is applied to the two levers 420, 421 they are prevented from moving into the housing by the abutment of the detents 428 with the bevelled surfaces 427. When the force applied to each lever 420, 421 reaches a pre-determined magnitude it is sufficient to deflect the side walls of the levers 420, 421 inwardly so allowing the detents 428 to ride across the bevelled surfaces 427 into the housing 409. A soon as the detents have passed over the bevelled surfaces 427 the levers 420, 421 are free to move towards the container 430 housed within the housing 409 so as to actuate the pump. Once again, this ensures that a reliable spray is produced.

When the force is released from the levers 420, 421 they are moved back towards their start positions but require the application of a small outward force in order to re-engage the detents 428 with the bevelled surfaces 427.

With particular reference to FIGS. 22 to 24 there is shown a fluid dispensing device 505 having a housing 509 for housing a fluid discharge device 508. The housing has a nozzle 511 extending out from one end for engagement with a body orifice such as a nasal cavity.

The fluid discharge device is conventional in nature and as is previously described having a container 530 for the fluid to be dispensed, a compression pump fixed within the container 530 and a discharge tube 531 extending out from the pump to deliver fluid to an orifice 515 formed in the nozzle 511. As previously described the pump is actuated by pushing the discharge tube 531 into the pump, which is achieved by moving the container 530 towards the nozzle 511.

A finger operable means is provided to move the container 530, the finger operable means is in the form of a lever 520 slidably supported within the housing 509 to apply a force to the container 530 so as to move the container 530 towards the nozzle 511 and actuate the compression pump.

The lever 520 has two flanges each of which is slidably supported by means of rails 555, 556 that are engaged with U-shaped guides 557 formed in the housing 509.

A pre-load means is provided to prevent the pump being actuated before a pre-determined force is applied to the lever 520.

The pre-load means comprises of a spring 558 interposed between the lever 520 and the container 530 and a latching means 560, 561. The spring 558 is used to urge the container 530 towards the nozzle 511 so as to actuate the compression pump.

The spring is interposed between a collar 540 connected to the container 530 and a base plate 541. A transfer rod 542 extends out from each side of the base plate for engagement with an inclined surface 543 formed on each flange of the lever 520. When the lever 520 is pushed or urged by a user towards the container 530 the transfer rods 542 move up the inclined surfaces 543 thereby compressing the spring 558. However, the container 530 is not moved because the collar 540 is connected to the housing 509 by the latching means 560, 561.

The latching means comprises of a rib 560 formed on an internal wall of the housing 509 and two outwardly extending arm 561 connected to the collar 540.

Each of the arms 561 is connected to the collar via a living hinge 563 so that when the collar 540 moves towards the nozzle 511 the arms 561 are able to abut against the collar 540 and so transfer load to the rib 560 but when the collar 540 is moving away from the nozzle 511 the arms 561 are able to flip up so as to allow them to pass freely over the rib 560. A return spring 565 is provided to return the lever 520 to its normal rest position when no force is being applied to it.

Operation of the fluid dispensing device is as follows.

The application of an initial force to the lever 520 causes the spring 558 to be compressed by the movement of the lever 520 without any movement of the container 530 occurring due to the engagement of the arms 561 with the rib 560. This will continue until a pre-determined force is applied, at which point the means used to prevent actuation of the compression pump, that is to say the arms 561 and the rib 560, are overcome by the force being applied to the container 530 by the spring 558 and the container 530 moves rapidly towards the nozzle 511 so as to actuate the compression pump.

Upon releasing the force from the lever 520 it is returned to its rest position by the return spring 565 and a spring within the pump returns the container back to its rest position so that the arms 561 re-engage with the rib 560.

The use of a spring to move the container has the advantage that a known force is used to move the container and so a consistent spray can be produced.

It will be appreciated that although the invention has been described with respect to several specific embodiments there are many alternative combinations and arrangements that could be used. The primary objective of the invention is to provide a fluid dispensing device that is operable by one or more levers applying a force to a container transversely with respect to a longitudinal axis of the container and which includes some pre-load mechanism or means to prevent the container from being significantly moved until the force being applied to it reaches a pre-determined magnitude known to produce a reliable high quality spray.

Administration of medicament may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. Embodiments are envisaged in which combinations of medicaments are employed.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone (e.g. as the furoate ester), ciclesonide, triamcinolone (e.g. as the acetonide), 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester or 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; PDE4 inhibitors e.g. cilomilast or roflumilast; leukotriene antagonists e.g. montelukast, pranlukast and zafirlukast; [adenosine 2a agonists, e.g. 2R,3R,4S,5R)-2-[6-Amino-2-(1S-hydroxymethyl-2-phenyl-ethylamino)-purin-9-yl]-5(2-ethyl-2H-tetrazol-5-yl)-tetrahydro-furan-3,4-diol (e.g. as maleate)]*; [α4 integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy) acetyl]amino}pentanoyl)amino]propanoic acid (e.g as free acid or potassium salt)]*, diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: 6α,9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α,9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicament is formulated as any suitable fluid formulation, particularly a solution (e.g. aqueous) formulation or a suspension formulation, optionally containing other pharmaceutically acceptable additive components.

Suitable formulations (e.g. solution or suspension) may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

Suitable formulations (e.g. solution or suspension) may comprise one or more excipients. By the term "excipient", herein, is meant substantially inert materials that are nontoxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, and combinations thereof.

Suitable carbohydrates include monosaccharides include fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof;

Suitable solution formulations may comprise a solubilising agent such as a surfactant. Suitable surfactants include α-[4-(1,1,3,3-tetramethylbutyl)phenyl]-ω-hydroxypoly (oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (e.g. PEG 200) and propylene glycol; sugars such as dextrose; and ethanol. Dextrose and polyethylene glycol (e.g. PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solublising agents such as polysorbate, glycerine, benzyl alcohol, polyoxyethylene castor oils derivatives, polyethylene glycol and polyoxyethylene alkyl ethers (e.g. Cremophors, Brij).

Suitable solution formulations may also comprise one or more of the following components: viscosity enhancing agents; preservatives; and isotonicity adjusting agents.

Suitable viscosity enhancing agents include carboxymethylcellulose, veegum, tragacanth, bentonite, hydroxypropylmethylcellulose, hydroxypropylcellulose, hydroxyethylcellulose, poloxamers (eg. poloxamer 407), polyethylene glycols, alginates xanthym gums, carageenans and carbopols.

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable suspension formulations comprise an aqueous suspension of particulate medicament and optionally suspending agents, preservatives, wetting agents or isotonicity adjusting agents.

The particulate medicament suitably has a mass mean diameter (MMD) of less than 20 μm, preferably between 0.5-10 μm, especially between 1-5 μm. If particle size reduction is necessary, this may be achieved by techniques such as micronisation and/or microfluidisation.

Suitable suspending agents include carboxymethylcellulose, veegum, tragacanth, bentonite, methylcellulose and polyethylene glycols.

Suitable wetting agents function to wet the particles of medicament to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable preservatives and isotonicity adjusting agents are as described above in relation to solution formulations.

The dispensing device herein is suitable for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 μg, 50 μg, 100 μg, 200 μg or 250 μg of active medicament. The precise dosage is either known or readily ascertainable by those skilled in the art.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims.

The invention claimed is:

1. A fluid dispensing device for spraying a fluid into a body cavity comprising a housing, a nozzle at an upper end of the device for insertion into a body cavity, a fluid discharge device moveably housed within the housing, the fluid discharge device having a longitudinal axis and comprising a container for storing the fluid to be dispensed and a compression pump having a suction inlet located within the container and a discharge tube extending along the longitudinal axis for transferring fluid from the pump to the nozzle and at least one finger-operable lever pivotally supported at a lower end thereof on the housing so as to be pivotable into the housing, transversely with respect to the longitudinal axis of the fluid discharge device, from a rest position to an actuated position to apply a force to an actuating member connected to a neck of the container to cause the container to move upwards along the longitudinal axis towards the nozzle so as to actuate the compression pump, wherein a pre-load is formed between the at least one lever and the actuating member to prevent pivoting of the at least one lever from the rest position to the actuated position for actuation of the compression pump until a predetermined force is applied to the at least one lever, wherein the actuating member and the at least one lever have surfaces which slidingly interact when the at least one lever pivots from the rest position to the actuated position to cause the container to move upwards along the longitudinal axis, wherein the pre-load is formed by one of the surfaces having first and second surface portions on which the other surface successively slides as the at least one lever pivots from the rest position to the actuated position, and wherein the first surface portion is steeper than the second surface portion.

2. A fluid dispensing device as claimed in claim 1 wherein said container contains a volume of fluid medicament formulation.

3. A fluid dispensing device as claimed in claim 2, wherein said fluid medicament formulation is in the form of a solution formulation.

4. A fluid dispensing device as claimed in claim 2, wherein said fluid medicament formulation is in the form of a suspension formulation.

5. A fluid dispensing device as claimed in claim 2, wherein the fluid medicament formulation comprises an anti-inflammatory medicament compound.

6. A fluid dispensing device as claimed in claim 5, wherein said medicament compound is a glucocorticoid compound.

7. A fluid dispensing device as claimed in claim 6, wherein said glucocorticoid compound is selected from the group consisting of 6α, 9α-Difluoro-17α-(1-oxopropoxy)-11β-hydroxy-16α-methyl-3-oxo-androsta-1,4-diene-17β-carbothioic acid S-fluoromethyl ester; 6α, 9α-difluoro-17α-[(2-furanylcarbonyl)oxy]-11β-hydroxy-16α-methyl-3-oxo-androsta-1,4-diene-17β-carbothioic acid S-fluoromethyl ester; and 6α, 9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

8. A fluid dispensing device as claimed in claim 2, wherein the fluid medicament formulation comprises a medicament compound selected from the group consisting of PDE4 inhibitors, leukotriene antagonists, iNOS inhibitors, tryptase and elastase inhibitors, beta-2 integrin antagonists and adenosine 2a agonists.

9. A fluid dispensing device as claimed in claim 1, wherein the actuating member is connected to the container neck by a collar.

10. A fluid dispensing device as claimed in claim 1, wherein the actuating member and the housing comprising mating guides for guiding longitudinal movement of the container during actuation.

11. A fluid dispensing device as claimed in claim 1, wherein the first surface portion is inclined at a lesser angle to the longitudinal axis than the second surface portion.

12. A fluid dispensing device as claimed in claim 1 configured as a nasal inhaler.

13. A fluid dispensing device as claimed in claim 11, wherein the surface of the actuating member has the first and second surface portions.

14. A fluid dispensing device as claimed in claim 1, wherein the at least one lever is repeatedly movable between the rest and actuated positions for repeated actuation of the compression pump.

15. A fluid dispensing device as claimed in claim 1, wherein the nozzle is aligned with the longitudinal axis.

16. A fluid dispensing device as claimed in claim 15, wherein the nozzle is disposed on the housing.

17. A fluid dispensing device as claimed in claim 1, wherein the surface of the at least one lever is spaced upwardly from its pivot point.

18. A fluid dispensing device as claimed in claim 17, wherein the surface of the at least one lever is provided at an upper end of the at least one lever.

19. An actuating system for a fluid dispensing device for dispensing a fluid from a dispensing container, the system comprising:

an actuating member for connection to a neck of the dispensing container, a housing having an upper end and an axis, wherein the housing is adapted to house the dispensing container for movement along said axis, and at least one finger-operable lever pivotally mounted at a lower end thereof on the housing so as to be pivotable into the housing, transversely with respect to the axis, from a rest position to an actuated position to apply a force to the actuating member, when the dispensing container is present in the housing with the actuating member connected to the neck, to move the dispensing container upwards along the axis so as to cause dispensing of fluid from the dispensing container, wherein a pre-load is formed between the at least one lever and the actuating member to prevent pivoting of the at least one lever from the rest position to the actuated position and dispensing from the dispensing container until a pre-determined force is applied to the at least one lever, wherein the actuating member and the at least one lever have surfaces which are adapted in use to slidingly interact when the at least one lever pivots from the rest position to the actuated position to move the dispensing container upwards along the axis, wherein the pre-load is formed by one of the surfaces having first and second surface portions on which the other surface is adapted in use to successively slide as the at least one lever pivots from the rest position to the actuated position, and wherein the first surface portion is steeper than the second surface portion.

20. An actuating system as claimed in claim 19, wherein the first surface portion is inclined at a lesser angle to the axis than the second surface portion.

21. An actuating system as claimed in claim 19, wherein the surface of the actuating member has the first and second surface portions.

22. An actuating system as claimed in claim 19, wherein the at least one lever is repeatedly movable between the rest and actuated positions for repeated actuation of the dispensing container.

23. An actuating system as claimed in claim 19, wherein the surface of the at least one lever is spaced upwardly from its pivot point.

24. An actuating system as claimed in claim 19, wherein the surface of the at least one lever is provided at an upper end of the at least one lever.

25. An actuating system as claimed in claim 19, wherein the housing further has a nozzle for insertion into a body cavity.

26. An actuating system as claimed in claim 25, wherein the body cavity is a human nostril.

27. An actuating system as claimed in claim 25, wherein the nozzle is disposed on the upper end of the housing 28. An actuating system as claimed in claim 25 wherein the nozzle is aligned with the axis.

29. A fluid dispensing device comprising an actuating system as claimed in claim 19 and further comprising the dispensing container mounted in the housing with the actuating member connected to a neck of the dispensing container.

30. A fluid dispensing device as claimed in claim 29, wherein the dispensing container comprises a pump which is actuated when the dispensing container is moved upwards along the axis.

31. A fluid dispensing device as claimed in claim 29, wherein the dispensing container has a longitudinal axis which extends parallel to the axis.

32. A fluid dispensing device as claimed in claim 29, wherein the dispensing container is compressed when it moves upwardly along the axis to dispense fluid therefrom.

33. A fluid dispensing device for dispensing a fluid from a dispensing container comprising:
   a housing having an upper end,
   a dispensing container movably housed in the housing for movement along a longitudinal axis of the dispensing container, and
   at least one finger-operable lever pivotally mounted at a lower end thereof on the housing so as to be pivotable into the housing, transversely with respect to the longitudinal axis, from a rest position to an actuated position to apply a force to the dispensing container to move the dispensing container upwardly along the longitudinal axis so as to cause dispensing of fluid from the dispensing container,
   wherein a pre-load is formed between the at least one lever and the dispensing container to prevent pivoting of the at least one lever from the rest position to the actuated position and dispensing from the dispensing container until a pre-determined force is applied to the at least one lever,
   wherein the dispensing container and the at least one lever have surfaces which are adapted to slidingly interact when the at least one lever pivots from the rest position to the actuated position to move the dispensing container upwards along the longitudinal axis,
   wherein the pre-load is formed by one of the surfaces having first and second surface portions on which the other surface is adapted to successively slide as the at least one lever pivots from the rest position to the actuated position, and
   wherein the first surface portion is steeper than the second surface portion.

34. A fluid dispensing device as claimed in claim 33, wherein the surface of the dispensing container is presented by an actuating member connected to a neck of the dispensing container.

35. A fluid dispensing device as claimed in claim 33, wherein the first surface portion is inclined at a lesser angle to the axis than the second surface portion.

36. A fluid dispensing device as claimed in claim 34, wherein the surface of the actuating member has the first and second surface portions.

37. A fluid dispensing device as claimed in claim 33, wherein the at least one lever is repeatedly movable between the rest and actuated positions for repeated actuation of the dispensing container.

38. A fluid dispensing device as claimed in claim 33, wherein the surface of the at least one lever is spaced upwardly from its pivot point.

39. A fluid dispensing device as claimed in claim 33, wherein the surface of the at least one lever is provided at an upper end of the at least one lever.

40. A fluid dispensing device as claimed in claim 33, wherein the housing further has a nozzle for insertion into a body cavity.

41. A fluid dispensing device as claimed in claim 40, wherein the body cavity is a human nostril.

42. A fluid dispensing device as claimed in claim 40, wherein the nozzle is disposed on the upper end of the housing.

43. A fluid dispensing device as claimed in claim 33, wherein the dispensing container comprises a pump which is actuated when the dispensing container is moved upwards along the axis.

44. A fluid dispensing device as claimed in claim 33, wherein the dispensing container is compressed when it is moved upwardly along the axis to dispense fluid therefrom.

45. A fluid dispensing device as claimed in claim 42, wherein the nozzle is aligned with the longitudinal axis.

* * * * *